US006221839B1

(12) United States Patent
Alitalo et al.

(10) Patent No.: US 6,221,839 B1
(45) Date of Patent: Apr. 24, 2001

(54) FIT4 LIGAND AND METHODS OF USE

(75) Inventors: Kari Alitalo, Espoo; Vladimir Joukov, Helsinki, both of (FI)

(73) Assignees: Helsinki University Licensing Ltd. Oy, Helsinki (FI); Ludwig Institute for Cancer Research, New York ( * ) Notice: Subject to any disclaimer, the term of this patent is extended or adjusted under 35 U.S.C. 154(b) by 0 days.

(21) Appl. No.: 08/510,133

(22) Filed: Aug. 1, 1995

(51) Int. Cl.[7] .......................... A61K 38/18; C07K 14/475
(52) U.S. Cl. ................................ 514/12; 514/2; 530/399
(58) Field of Search .................................. 530/399; 514/2, 514/21

(56) References Cited

U.S. PATENT DOCUMENTS

| 5,219,739 | * | 6/1993 | Tischer et al. ...................... 435/69.4 |
| 5,326,695 | | 7/1994 | Andersson et al. . |
| 5,332,671 | * | 7/1994 | Ferrara et al. ..................... 435/240.1 |
| 5,932,540 | | 8/1999 | Hu et al. . |
| 5,935,820 | | 8/1999 | Hu et al. . |

FOREIGN PATENT DOCUMENTS

| 0 506 477 A1 | 3/1992 | (EP) . |
| 9524473 | * 9/1995 | (WO) . |
| WO 95/33050 A1 | 12/1995 | (WO) . |
| WO 95/33772 | 12/1995 | (WO) . |
| WO 96/11269 A2 | 4/1996 | (WO) . |
| WO 96/30046 A1 | 10/1996 | (WO) . |
| WO 96/39421 A1 | 12/1996 | (WO) . |
| WO 96/39515 A1 | 12/1996 | (WO) . |
| 97/05250 | 2/1997 | (WO) . |
| 97/09427 | 3/1997 | (WO) . |
| 97/17442 | 5/1997 | (WO) . |

OTHER PUBLICATIONS

Sitaras et al. Constitutive production of platelet–derived growth factor–like proteins by human prostate carcinoma cell lines. Cancer Research. vol. 48, No. 7, pp. 1930–1935, Apr. 1, 1988.*

Fournier et al. Mutation at tyrosine residue 1337 abrogates ligand–dependent transforming capacity of the FLT4 receptor. Oncogene. vol. 11, No. 5, pp. 921–931, Sep. 7, 1995.*

Pajussla et al. Signalling properties of FLT4, a proteolytically processed receptor tyrosine kinase related to two VEGF receptors. Oncogene. vol. 9, No. 12, pp. 3545–3555.*

Galland et al. The FLT4 gene encodes a transmembrane tyrosine kinase related to the vascular endothelial growth factor receptor. Oncogene. vol. 8, No. 5, pp. 1233–1240, May 1993.*

U.S. application No. 08/207,550, Jing–Shan Hu et al., filed Mar. 8, 1994.

U.S. application No. 08/465,968, Crain Rosen et al., filed Jun. 6, 1995.

U.S. application No. 60/003,491, James Lee et al., filed Sep. 8, 1995.

U.S. application No. 08/554,374, Lyman, S., filed Nov. 8, 1995.

Achen, M.G. et al., "Vascular Endothelial Growth Factor D (VEGF–D) is a Ligand for the Tyrosine Kinases VEGF Receptor 2 (Flk1) and VEGF Receptor 3 (Flt4)," *Proceedings of the National Academy of Science*, USA, 95:548–553 (Jan., 1998).

Adams, M.D. et al., "Initial assessment of human gene diversity and expression patterns based upon 83 million nucleotides of cDNA sequence," *Nature*, 377(6547 Supplement):3–174 (Sep., 1995).

Cohen, T. et al., "VEGF121, A Vascular Endothelial Growth Factor (VEGF) Isoform Lacking Heparin Binding Ability, Requires Cell–Surface Heparan Sulfates for Efficient Binding to the VEGF Receptors of Human Melanoma Cells," *Journal of Biological Chemistry*, 270(19):11322–11326 (May 12, 1995).

Genbank AA151613, "z127h03.s1 Soares pregnant uterus NbHPU *Homo sapiens* cDNA clone 503189 3'," Hillier, L. et al., Dated May 14, 1997.

Genbank AA425486, "zw46b06.r1 Soares total fetus Nb2HF8 9w *Homo sapiens* cDNA clone 773075 5' similar to SW:VEGF_Mouse Q00731 Vascular Endothelial Growth Factor Precursor," Deposited by Hillier, L. et al. Dated Oct. 16, 1997.

Genbank N31713, "yy15b12.s1 *Homo sapiens* cDNA clone 271295 3'," Deposited by Hillier, L. et al. Dated Jan. 10, 1996.

Genbank N31720, "yy15d12.s1 *Homo sapiens* cDNA clone 271319 3'," Deposited by Hillier, L. et al. Dated Jan. 10, 1996.

Genbank AA406492, "zv12g06.r1 Soares NhHMPu S1 *Homo sapiens* cDNA clone 75366 5'," Deposited by Hillier, L. et al. Dated May 17, 1997.

Genbank N50972, "yy94b08.s1 *Homo sapiens* cDNA clone 281175 3'," Deposited by Hillier, L. et al. Dated Feb. 14, 1996.

Genbank AA421713, "zu24b03.s1 Soares NhHMPu S1 *Homo sapiens* cDNA clone 738893 3'," Deposited by Hillier, L. et al. Dated Oct. 16, 1997.

Genbank N94399, "zb76f04.s1 Soares senescent fibroblasts NbHSF *Homo sapiens* cDNA clone 309535 3'," Deposited by Hillier, L et al. Dated Aug. 20, 1996.

Genbank H05177, "y185b08.r1 *Homo sapiens* cDNA clone 44993 5'," Deposited by Hillier, L. et al. Dated Jun. 21, 1995.

(List continued on next page.)

Primary Examiner—Christine Saoud
(74) Attorney, Agent, or Firm—Marshall, O'Toole, Gerstein, Murray & Borun

(57) ABSTRACT

Provided are ligands for the receptor tyrosine kinase, Flt4. Also provided are cDNAs and vectors encoding the ligand, pharmaceutical compositions and diagnostic reagents.

29 Claims, 16 Drawing Sheets

OTHER PUBLICATIONS

Genbank AA479987, "zv18h12.s1 Soares NhHMPu S1 *Homo sapiens* cDNA clone 754055 3'," Deposited by Hillier, L. et al. Dated Aug. 8, 1997.

Genbank H05134, "y185b08.s1 *Homo sapiens* cDNA clone 44993 3'," Deposited by Hillier, L. et al. Dated Jun. 21, 1995.

Genbank, AA298182 "EST113866 Bone VII *Homo sapiens* cDNA 5' end," Deposited by Adams, M.D. et al. Dated Apr. 18, 1997.

Genbank AA298283, "EST113896 Bone VII *Homo sapiens* cDNA 5' end similar to similar to vascular endothelial growth factor," Deposited by Adams, M.D. et al. Dated Apr. 18, 1997.

Genbank T81481, "yd29f07.s1 *Homo sapiens* cDNA clone 109669 3'," Deposited by Hillier, L. et al. Dated Mar. 15, 1995.

Genbank AA425303, "zw46b06.s1 Soares total fetus Nb2HF8 9w *Homo sapiens* cDNA clone 773075 3', mRNA sequence," Deposited by Hillier, L. et al. Dated Oct. 16, 1997.

Genbank Z40230, "*H. sapiens* partial cDNA sequence; clone c–1wf11," Deposited by Genexpress. Dated Sep. 21, 1995.

Genbank Z44272, "*H. sapiens* partial cDNA sequence; clone c–1wf11," Deposited by Genexpress. Dated Sep. 21, 1995.

Genbank AA478766, "zv18h12.r1 Soares NhHMPu S1 *Homo sapiens* cDNA clone 754055 5'," Deposited by Hillier, L. et al. Dated Aug. 8, 1997.

Genbank H96876, "yw04b12.s1 Soares melanocyte 2NbHM *Homo sapiens* cDNA clone 251231 3'," Deposited by Hillier, L. et al. Dated Nov. 25, 1996.

Genbank H96533, "yw04b12.r1 Soares melanocyte 2NbHM *Homo sapiens* cDNA clone 251231 5'," Deposited by Hillier, L. et al. Dated Nov. 25, 1996.

Genbank T81690, "yd29f07.r1 *Homo sapiens* cDNA clone 109669 5' similar to SP:BAR3_Chite Q03376 Balbiani Ring Protein 3," Deposited by Hillier, L. et al. Dated Mar. 15, 1995.

Genbank T84377, "yd37h08.r1 *Homo sapiens* cDNA clone 110463 5' similar to SP:BAR3_Chite Q03376 Balbiani Ring Protein 3," Deposited by Hillier, L. et al. Dated Mar. 16, 1995.

Genbank N42368, "yy15b11.r1 *Homo sapiens* cDNA clone 271293 5'," Deposited by Hillier, L. et al. Dated Jan. 25, 1996.

Genbank N42374, "yy15d11.r1 *Homo sapiens* cDNA clone 271317 5'," Deposited by Hillier, L. et al. Dated Jan. 25, 1996.

Genbank H81868, "yv83d09.s1 *Homo sapiens* cDNA clone 249329 3'," Deposited by Hillier, L. et al. Dated Nov. 9, 1995.

Genbank H81867, "yv83d09.r1 *Homo sapiens* cDNA clone 249329 5'," Deposited bu Hillier, L. et al. Dated Nov. 9, 1995.

Genbank AA149461, "z127h03.r1 Soares pregnant uterus NbHPU *Homo sapiens* cDNA clone 503189 5' similar to SW:BAR3_Chite Q03376 Balbiani Ring Protein 3 Precursor," Deposited by Hillier, L. et al. Dated May 14, 1997.

Genbank R77495, "yi79e04.s1 *Homo sapiens* cDNA clone 145470 3'," Deposited by Hillier, L. et al. Dated Jun. 7, 1995.

Genbank H07899, "y186g06.s1 *Homo sapiens* cDNA clone 45138 3'," Deposited by Hillier, L. et al. Dated Jun. 23, 1995.

Genbank T89295, "yd37h08.s1 *Homo sapiens* cDNA clone 110463 3'," Deposited by Hillier, L. et al. Dated Mar. 20, 1995.

Genbank C21512, "HUMGS0010510, Human Gene Signature, 3'–directed cDNA sequence," Deposited by Okubo, K. Dated Oct. 1, 1996.

Genbank N82975, "TgESTzy53h10.r1 TgRH Tachyzoite cDNA Toxoplasma gondii cDNA clone tgzy53h10.r1 5'," Deposited by Hehl, A. et al. Dated Sep. 10, 1997.

Genbank AA285997, "vb88h06.r1 Soares mouse 3NbMS Mus musculus cDNA clone 764123 5'," Deposited by Marra, M. et al. Dated Apr. 9, 1997.

Genbank AA549856, "0929m3 gmbPfHB3.1, G. Roman Reddy Plasmodium falciparum genomic clone 0929m," Deposited by Dame, J.B. et al. Dated Aug. 11, 1997.

Jeltsch, M. et al., "Hyperplasia of Lymphatic Vessels in VEGF–C Transgenic Mice," *Science*, 276:1423–1425 (May, 1997).

Joukov, V. et al., "Proteolytic Processing Regulates Receptor Sepcificity and Activity of VEGF–C," *EMBO Journal*, 16(13):3898–3911 (Jun., 1997).

Joukov, V. et al., "A Recombinant Mutant Vascular Endothelial Growth Factor–C that has Lost Vascular Endothelial Growth Factor Receptor–2 Binding, Activation, and Vascular Permeability Activities," *Journal of Biological Chemistry*, 273(12):6599–6602 (Mar. 20, 1998).

Lee, J. et al., "Vascular Endothelial Growth Factor Related Protein (vrp): A Ligand and Specific Activator of the Tyrosine Kinase Receptor Flt4," EMBL Sequence Data Library, XP002066361, accession No. U4142. Dated Jan. 10, 1996.

Hillier et al., "The WashU–Merch EST Project," EMBL Database entry HS991157, accession No. H07991, Jul. 2, 1995.

Alitalo et al., "Vascular Endothelial Growth Factors and Receptors Involved in Angiogenesis," *The 9th International Conference of the International Society of Differentiation (ISD), Development Cell Differentiation and Cancer*, Pisa (Italy), Sep. 28–Oct. 2, 1996, p. 66 (Abstract S22).

Alitalo et al., "Vascular Endothelial Growth Factors B and C Receptors Involved in Angiogenesis," *German–American Academic Council Foundation(GAAC)/ Stiftung Deutsch–Amerikanisches Akademisches Konzil (DAAK), 2nd Symposium on Current Problems in Molecular Medicine: The Role of Cytokines in Human Disease*, Nov. 17–20, 1996, Ringberg Castle, Germany, p. 1 (Abstract).

Andersson et al., "Assignment of Interchain Disulfide Bonds in platelet–Derived Growth Factor (PDGF) and Evidence for Agonist Activity of Monomeric PDGF," *J. Biol. Chem.*, 267(16):11260–11266 (Jun. 5, 1992).

Aprelikova et al., "FLT4, A Novel Class III Receptor Tyrosine Kinase in Chromosome 5q33–qter," *Cancer Research*, 52:746–748 (Feb. 1, 1992).

Basilico et al., "The FGF Family of Growth Factors and Oncogenes," *Adv. Cancer Res.*, 59:145–165 (1992).

Berse et al., "Vascular Permeability Factor (Vascular Endothelial Growth Factor) Gene is Expressed Differentially in Normal Tissues, Macrophages, and Tumors," *Mol. Biol. Cell.*, 3:211–220 (Feb., 1992).

Betsholtz et al., "cDNA Sequence and Chromosomal Localization of Human Platelet–Derived Growth Factor A–Chain and Its Expression in Tumor Cell Lines," *Nature*, 320:695–699 (Apr., 1986).

Borg et al., "Biochemical Characterization of Two Isoforms of FLT4, a VEGF Receptor–Related Tyrosine Kinase," *Oncogene*, 10:973–84 (1995).

Cao et al., "Heterodimers of Placenta Growth Factor/Vascular Endothelial Growth Factor," *J. Biol. Chem.*, 271(6):3154–3162 (Feb. 9, 1996).

Cheng and Flanagan, "Identification and Cloning of ELF–1, A Developmentally Expressed Ligand for the Mek4 and Sek Receptor Tyrosine Kinases," *Cell*, 79:157–168 (Oct. 7, 1994).

Claesson–Welsh et al., "Identification and Structural Analysis of the A Type Receptor for Platelet–derived Growth Factor," *J. Biol. Chem.*, 264(3):1742–1747 (Jan. 25, 1989).

Coffin et al., "Angioblast Differentiation and Morphogenesis of the Vascular Endothelium in the Mouse Embryo," *Devel. Biol.*, 148:51–62 (1991).

Curran and Franza, "Fos and Jun: The AP–1 Connection," *Cell*, 55:395–397 (Nov. 4, 1988).

De Vries et al., "The fms–Like Tyrosine Kinase, a Receptor for Vascular Endothelial Growth Factor," *Science*, 255:989–991 (Feb. 21, 1992).

DiSalvo et al., "Purification and Characterization of a Naturally Occurring Vascular Endothelial Growth Factor: Placenta Growth Factor Heterodimer," *J. Biol. Chem.*, 270(13):7717–7723 (Mar. 31, 1995).

Dumont et al., "Dominant–negative and Targeted Null Mutations in the Endothelial Receptor Tyrosine Kinase, tek, Reveal a Critical Role in Vasculogenesis of the Embryo," *Genes Dev.*, 8:1897–1909 (1994).

Dumont et al., "Vascularization of the Mouse Embryo: A Study of flk–1, tek, tie and Vascular Endothelial Growth Factor Expression During Development," *Development Dynamics*, 203:80–92 (1995).

Dvorak et al., "Review: Vascular Permeability Factor/Vascular Endothelial Growth Factor, Microvascular Hyperpermeability, and Angiogenesis," *Amer. J. Path.*, 146:1029–1039 (1995).

Eichmann et al., "Two Molecules Related to the VEGF Receptor are Expressed in Early Endothelial Cells During Avian Embryonic Development," *Mech. Dev.*, 42:33–48 (1993).

Ferrara et al., "Molecular and Biological Properties of the Vascular Endothelial Growth Factor Family of Proteins," *Endocrine Rev.*, 13(1):18–32 (1992).

Finnerty et al., "Molecular Cloning of Murine FLT and FLT4," *Oncogene*, 8(11):2293–2298 (1993).

Flamme et al., "Vascular Endothelial Growth Factor (VEGF) and VEGF–Receptor 2 (flk–1) are Expressed During Vasculogenesis and Vascular Differentiation in the Quail Embryo," *Devel. Biol.*, 169:699–712 (1995).

Flanagan and Leder, "The kit Ligand: A Cell Surface Molecule Altered in Steel Mutant Fibroblasts," *Cell*, 63:185–194 (Oct. 5, 1990).

Folkman, "Angiogenesis in Cancer, Vascular, Rheumatoid and Other Disease," *Nature Med.*, 1(1):27–31 (1995).

Folkman et al., "Long–term Culture of Capillary Endothelial Cells," *Proc. Nat'l Acad. Sci., USA*, 76(10):5217–5221 (Oct., 1979).

Fong et al., "Role of the Flt–1 Receptor Tyrosine Kinase in Regulating the Assembly of Vascular Endothelium," *Nature*, 376:66–70 (Jul. 6, 1995).

Friesel et al., "Molecular Mechanisms of Angiogenesis: Fibroblast Growth Factor Signal Transduction," *FASEB J.*, 9:919–25 (1995).

Genbank S66407, "FLT4 Receptor Tyrosine Kinase Isoform FLT4 Long (3' Region, Alternatively Spliced) [Human, mRNA Partial, 216 nt].," Deposited by Pajusola et al., Dated Dec. 17, 1993.

Genbank U48800, "Mus Musculus Vascular Endothelial Growth Factor B Precursor (VEGF–B) mRNA, Complete Cds.," Deposited by Olofsson et al., Dated Aug. 19, 1996.

Genbank X15997, "Human Vascular Permeability Factor mRNA, Complete Cds.," Deposited by Keck et al., Dated Jun. 15, 1990.

Genbank X60280, "Vector Plasmid pLTRpoly DNA.," Deposited by Maekelae, T.P., Dated Jul. 16, 1996.

Genbank X68203, "*H. sapiens* mRNA for FLT4, Class III Receptor Tyrosine Kinase.," Deposited by Aprelikova, O., Dated Nov. 30, 1993.

Genbank X94216, "*Homo sapiens* mRNA for VEGF–C protein," Deposited by Joukov et al., Dated Feb. 6, 1996.

Harlow et al., *Antibodies, a Laboratory Manual*, Cold Spring Harbor Laboratory Press, pp. 72–137, 141–157, 287 & 321–358 (1988).

Heldin et al., "Structure of Platelet–Derived Growth Factor: Implications Functional Properties," *Growth Factors*, 8:245–252 (1993).

Joukov et al., "A Novel Vascular Endothelial Growth Factor, VEGF–C, Is a Ligand for the Flt4 (VEGFR–3) and KDR (VEGFR–2) Receptor Tyrosine Kinases," *EMBO J.*, 15(2):290–298 (1996).

Kaipainen et al., "Expression of the FMS–Like Tyrosine Kinase 4 Gene Becomes Restricted to Lymphatic Endothelium During Development," *Proc. Nat'l Acad. Sci., USA*, 92:3566–3570 (Apr., 1995).

Kaipainen et al., "The Related FLT4, FLT1 and KDR Receptor Tyrosine Kinases Show Distinct Expression Patterns in Human Fetal Endothelial Cells," *J. Exp. Med.*, 178:2077–2088 (Dec., 1993).

Kaipainen et al., "Enhanced Expression of the Tie Receptor Tyrosine Kinase Messenger RNA in the Vascular Endothelium of Metastatic Melanomas," *Cancer Res.*, 54:6571–6577 (Dec. 15, 1994).

Kukk et al., "VEGF–C Receptor Binding and Pattern of Expression with VEGFR–3 Suggests a Role in Lymphatic Vascular Development," *Development*, 122:3829–3837 (1996).

Lee et al., "Vascular Endothelial Growth Factor–Related Protein: A Ligand and Specific Activator of the Tyrosine Kinase Receptor Flt4," *Proc. Nat'l Acad. Sci., USA*, 93:1988–1992 (Mar., 1996).

Leung et al., "Vascular Endothelial Growth Factor Is a Secreted Angiogenic Mitogen," *Science*, 246:1306–1309 (Dec. 8, 1989).

Levy et al., "Post–transcriptional Regulation of Vascular Endothelial Growth Factor by Hypoxia," *J. Biol. Chem.*, 271(5):2746–2753 (Feb. 2, 1996).

Levy et al., "Transcriptional Regulation of the Rat Vascular Endothelial Growth Factor Gene by Hypoxia," *J. Biol. Chem.*, 270(22):13333–13340 (Jun. 2, 1995).

Lyman et al., "Molecular Cloning of a Ligand for the flt3/ftk–2 Tyrosine Kinase Receptor: A Proliferative Factor for Primitive Hematopoietic Cells," *Cell*, 75:1157–1167 (Dec. 17, 1993).

Maglione et al., "Isolation of a Human Placenta cDNA Coding for a Protein Related to the Vascular Permeability Factor," *Proc. Nat'l Acad. Sci., USA*, 88:9267–9271 (Oct., 1991).

Maglione et al., "Two Alternative mRNAs Coding for the Angiogenic Factor, Placenta Growth Factor (PIGF) are Transcribed from a Single Gene of Chromosome 14," *Oncogene*, 8:925–931 (1993).

Matthews et al., "A Receptor Tyrosine Kinase cDNA Isolated from a Population of Enriched Primitive Hematopoietic Cells and Exhibiting Close Genetic Linkage to c–kit," *Proc. Nat'l Acad. Sci., USA*, 88:9026–9030 (Oct., 1991).

Metzelaar et al., "CD63 Antigen," *J. of Biol. Chem.*, 266(5):3239–3245 (Feb. 15, 1991).

Millauer et al., "Glioblastoma Growth Inhibited in vivo by a Dominant–Negative Flk–1 Mutant," *Nature*, 367:576–579 (Feb. 10, 1994).

Millauer et al., "High Affinity VEGF Binding and Developmental Expression Suggest Flk–1 as a Major Regulator of Vasculogenesis and Angiogenesis," *Cell*, 72:835–846 (Mar. 26, 1993).

Mitchell et al., "Transcription Factor AP–2 is Expressed in Neural Crest Cell Lineages During Mouse Embryogenesis," *Genes and Dev.*, 5:105–119 (1991).

Morgenstern et al., "Advanced Mammalian Gene Transfer: High Titre Retroviral Vectors With Multiple Drug Selection Markers and a Complementary Helper–Free Packaging Cell Line," *Nucl. Acids Res.*, 18(12):3587–3595 (1990).

Mount, S.M., "A Catalogue of Splice Junction Sequences," *Nucl. Acids Res.*, 10(2):459–472 (1982).

Mustonen et al., "Endothelial Receptor Tyrosine Kinases Involved in Angiogenesis," *J. Cell Biol.*, 129:895–898 (May, 1995).

Nelson and Sun, "The 50– and 58–kdalton Keratin Classes as Molecular Markers for Stratified Squamous Epithelia: Cell Culture Studies," *J. Cell Biol.*, 97:244–251 (Jul., 1983).

Neufeld et al., "Vascular Endothelial Growth Factor and Its Receptors," *Prog. Growth Fact. Res.*, 5:89–97 (1994).

Oefner et al., "Crystal Structure of Human Platelet–derived Growth Factor BB," *EMBO J.*, 11(11):3921–3926 (1992).

Oelrichs et al., "NYK/FLK–1: A Putative Receptor Tyrosine Kinase Isolated from E10 Embryonic Neuroepithelium is Expressed in Endothelial Cells of the Developing Embryo," *Oncogene*, 8:11–18 (1993).

Olofsson et al., "Vascular Endothelial Growth Factor B, A Novel Growth Factor for Endothelial Cells," *Proc. Nat'l Acad. Sci., USA*, 93:2576–2581 (Mar., 1996).

Paavonen et al., "Chromosomal Localization and Regulation of Human Vascular Endothelial Growth Factors B and C (VEGF–B and VEGF–C)," *IX International Vascular Biology Meeting*, Seattle, Washington, Sep. 4–8, 1996, p. 76 (Abstract 299).

Paavonen et al., "Novel Human Vascular Endothelial Growth Factor Genes VEGF–B and VEGF–C Localize to Chromosomes 11q13 and 4q34, Respectively," *Circulation* 93(6):1079–1082 (Mar. 15, 1996).

Park et al., "Placenta Growth Factor, Potentiation of Vascular Endothelial Growth Factor Bioactivity In vitro and In vivo, and High Affinity Binding to Flt–1 but not to Flk–1/KDR," *J. Biol. Chem.*, 269(41):25646–25654 (Oct. 14, 1994).

Partanen et al., "A Novel Endothelial Cell Surface Receptor Tyrosine Kinase with Extracellular Epidermal Growth Factor Homology Domains," *Mol. & Cell. Biol.*, 12(4):1698–1707 (Apr., 1992).

Partanen et al., "Putative Tyrosine Kinase Expressed in K–562 Human Leukemia Cells," *Proc. Nat'l Acad. Sci., USA*, 87:8913–8917 (Nov., 1990).

Paulsson et al., "The Balbiani Ring 3 Gene in *Chironomus tentans* has a Diverged Repetitive Structure Split by Many Introns," *J. Mol. Biol.*, 211:331–349 (1990).

Pear et al., "Production of High–titer Helper–free Retroviruses by Transient Transfection," *Proc. Nat'l Acad. Sci., USA*, 90:8392–8396 (Sep., 1993).

Pertovaara et al., "Vascular Endothelial Growth Factor Is Induced in Response to Transforming Growth Factor–β in Fibroblastic and Epithelial Cells," *J. Biol. Chem.*, 269(9):6271–6274 (Mar. 4, 1994).

Peters et al., "Vascular Endothelial Growth Factor Receptor Expression during Embryogenesis and Tissue Repair Suggests a Role in Endothelial Differentiation and Blood Vessel Growth," *Proc. Nat'l Acad. Sci., USA*, 90:8915–8918 (Oct., 1993).

Pötgens et al., "Covalent Dimerization of Vascular Permeability Factor/Vascular Endothelial Growth Factor Is Essential for Its Biological Activity," *J. Biol. Chem.*, 269(52):32879–32885 (Dec. 30, 1994).

Puri et al., "The Receptor Tyrosine Kinase TIE is Required for Integrity and Survival of Vascular Endothelial Cells," *EMBO J.*, 14:5884–5891 (1995).

Quinn et al., "Fetal Liver Kinase 1 is a Receptor for Vascular Endothelial Growth Factor and is Selectively Expressed in Vascular Endothelium," *Proc. Nat'l Acad. Sci., USA*, 90:7533–7537 (Aug., 1993).

Risau et al., "Platelet–Derived Growth Factor is Angiogenic In Vivo," *Growth Factors*, 7:261–266 (1992).

Risau, W., "Differentiation of Endothelium," *FASEB J.*, 9:926–933 (1995).

Sabin, F.R., "The Lymphatic System in Human Embryos, With A Consideration of the Morphology of the System as a Whole," *Am. J. Anat.*, 9(1):43–91 (1909).

Sambrook et al., *Molecular Cloning: a Laboratory Manual*, Second Edition, Cold Spring Harbor, New York: Cold Spring Harbor Laboratory (1989), pp. 2.60–2.79, 4.21–4.32, 7.3–7.36, and 9.47–9.51.

Sato et al., "Distinct Roles of the Receptor Tyrosine Kinases Tie–1 and Tie–2 in Blood Vessel Formation," *Nature*, 376:70–74 (Jul. 6, 1995).

Schneider et al., "A One–step Purification of Membrane Proteins Using a High Efficiency Immunomatrix," *J. Biol. Chem.*, 257(18):10766–70769 (Sep. 25, 1982).

Seetharam et al., "A Unique Signal Transduction from FLT Tyrosine Kinase, a Receptor for Vascular Endothelial Growth Factor VEGF," *Oncogene*, 10:135–147 (1995).

Senger et al., "Tumor Cells Secrete a Vascular Permeability Factor That Promotes Accumulation of Ascites Fluid," *Science*, 219:983–985 (Feb. 25, 1983).

Shalaby et al., "Failure of Blood–Island Formation and Vasculogenesis in Flk–1–deficient Mice," *Nature*, 376:62–66 (Jul. 6, 1995).

Shibuya et al., "Nucleotide Sequence and Expression of a Novel Human Receptor–Type Tyrosine Kinase Gene (flt) Closely Related to the fms Family," *Oncogene*, 5:519–524 (1990).

Shibuya, M., "Role of VEGF–FLT Receptor System in Normal and Tumor Angiogenesis," *Adv. Cancer Res.*, 67:281–316 (1995).

Shweiki et al., "Patterns of Expression of Vascular Endothelial Growth Factor (VEGF) and VEGF Receptors in Mice Suggest a Role in Hormonally Regulated Angiogenesis," *J. Clin. Invest.*, 91:2235–2243 (May, 1993).

Southern and Berg, "Transformation of Mammalian Cells to Antibiotic Resistance with a Bacterial Gene Under Control of the SV40 Early Region Promoter," *J. Mol. Appl. Genet.*, 1:327–341 (1982).

Terman et al., "Identification of New Endothelial Cell Growth Factor Receptor Tyrosine Kinase," *Oncogene*, 6:1677–1683 (1991).

Terman et al., "Identification of the KDR Tyrosine Kinase as a Receptor for Vascular Endothelial Cell Growth Factor," *Biochem. Biophys. Res. Commun.*, 187:1579–1586 (Sep. 30, 1992).

Terman et al., "VEGF Receptor Subtypes KDR and FLT1 Show Different Sensitivities to Heparin and Placenta Growth Factor," *Growth Factors*, 11(3):187–195 (1994).

Tischer et al., "The Human Gene for Vascular Endothelial Growth Factor. Multiple Protein Forms are Encoded Through Alternative Exon Splicing," *J. Biol. Chem.*, 266(18):11947–11954 (Jun. 25, 1991).

Vassar et al., "Tissue–specific and Differentiation –specific Expression of a Human K14 Keratin Gene in Transgenic Mice," *Proc. Nat'l Acad,. Sci., USA*, 86:1563–1567 (Mar., 1989).

Vassar et al., "Transgenic Mice Provide New Insights Into the Role of TGF–α During Epidermal Development and Differentiation," *Genes & Dev.*, 5:714–727 (1991).

Västrik et al., "Expression of the Mad Gene During Cell Differentiation In Vivo and Its Inhibition of Cell Growth In Vitro," *J. Cell. Biol.*, 128(6):1197–1208 (Mar., 1995).

von Heijne, G., "A New Method for Predicting Signal Sequence Cleavage Sites," *Nucleic Acids Res.*, 14(11):4683–4690 (1986).

Waltenberger et al., "Different Signal Transduction Properties of KDR and Flt1, Two Receptors for Vascular Endothelial Growth Factor," *J. Biol. Chem*, 269(43):26988–26995 (Oct. 28, 1994).

Wanaka et al., "Expression of FGF Receptor Gene in Rat Development," *Development*, 111:455–468 (1991).

Wen et al., "Neu Differentiation Factor: A Transmembrane Glycoprotein Containing an EGF Domain and an Immunoglobulin Homology Unit," *Cell* 69:559–572 (May 1, 1992).

Yamane et al., "A New Communication System Between Hepatocytes and Sinusoidal Endothelial Cells in Liver Through Vascular Endothelial Growth Factor and Flt Tyrosine Kinase Receptor Family (Flt–1 and KDR/Flk–1)," *Oncogene*, 9:2683–2690 (1994).

Ausprunk, et al., "Migration and Proliferation of Endothelial Cells in Preformed and Newly Formed Blood Vessels during Tumor Angiogenesis", *Microvascular Research*, 14:53–65 (1977).

Breier, et al., "Expression of vascular endothelial growth factor during embryonic angiogenesis and endothelial cell differentiation", *Development*, 114:521–532 (1992).

Dignam, et al., "Balbiani ring 3 in *Chironomus tentans* encodes a 185–kDa secretory protein which is synthesized throughout the fourth larval instar", *Gene*, 88:133–140 (1990).

Don, et al., "'Touchdown' PCR to circumvent spurious priming during gene amplification", *Nucleic Acids Research*, 19(14):4008 (1991).

Folkman, et al., "Angiogenesis", *The Journal of Biological Chemistry*, 267(16):10931–10934 (1992).

Kozak, "An analysis of 5'–noncoding sequences from 699 vertebrate messenger RNAs", *Nucleic Acids Research*, 15(20):8125–8148 (1987).

Mäkelä, et al., "Plasmid pLTRpoly: A Versatile High–Efficiency Mammalian Expression Vector", *Gene*, 118:293–294 (1992).

Pajusola, et al., "FLT4 Receptor Tyrosine Kinase Contains Seven Immunoglobulin–like Loops and Is Expressed in Multiple Human Tissues and Cell Lines", *Cancer Research*, 52:5738–5743 (1992).

Pajusola, et al., "Two human FLT4 receptor tyrosine kinase isoforms with distinct carboxy terminal tails are produced by alternative processing of primary transcripts", *Oncogene*, 8:2931–2937 (1993).

Risau, et al., "Changes in the Vascular Extracellular Matrix during Embryonic Vasculogenesis and Angiogenesis", *Developmental Biology*, 125:441–450 (1988).

Saksela, et al., "Cell–Associated Plasminogen Activation: Regulation and Physiological Functions", *Annu. Rev. Cell. Biol.*, 4:93–126 (1988).

Tessier, et al., "Enhanced secretion from insect cells of a foreign protein fused to the honeybee melittin signal peptide", *Gene*, 98:177–183 (1991).

van der Geer, et al., "Receptor Protein–Tyrosine Kinases and Their Signal Transduction Pathways", *Annu. Rev. Cell. Biol.*, 10:251–337 (1994).

* cited by examiner

```
                                                               MetThrValLeuTyrProGluTyr
GAGCAGTTACGGTCTCTGTGTCCAGTGTAGATGAACTCATGACTGTACTCTACCAGAATAT
         10              20              30              40              50

TrpLysMetTyrLysCysGlnLeuArgLysGlyGlyTrpGlnHisAsnArgGluGlnAla
TGGAAAATGTACAAGTGTCAGCTAAGGAAAGGAGGCTGGCAACATAACAGAGAACAGGCC
         70              80              90             100             110

AsnLeuAsnSerArgThrGluGluThrIleLysPheAlaAlaAlaHisTyrAsnThrGlu
AACCTCAACTCAAGGACACAGAAGAGACTATAAAATTTGCTGCAGCACATTATAATACAGAG
        130             140             150             160             170

IleLeuLysSerIleAspAsnGluTrpArgLysThrGlnCysMetProArgGluValCys
ATCTTGAAAAGTATTGATAATGAGTGGAGAAAGACTCAATGCCATGCCACGGGAGGTGT
        190             200             210             220             230

IleAspValGlyLysGluPheGlyValAlaAlaThrAsnThrPhePheLysProProCysVal
ATAGATGTGGGGAAGGAGTTTGGAGTCGCGACAAACACCTTCTTTAAACCTCCATGTGTG
        250             260             270             280             290

SerValTyrArgCysGlyGlyCysCysAsnSerGluGlyLeuGlnCysMetAsnThrSer
TCCGTCTACAGATGTGGGGGTTGCTGCAATGTGAGGGCTGCAGTGCATGAACACCAGC
        310             320             330             340             350

FIGURE 9A
```

ThrSerTyrLeuSerLysThrLeuPheGluIleThrValProLeuSerGlnGlyProLys
ACGAGCTACCTCAGCAAGACGTTATTTGAAATTACAGTGCCTCTCTTCAAGGCCCCAAA
     370                        390                        410

ProValThrIleSerPheAlaAsnHisThrSerCysArgCysMetSerLysLeuAspVal
CCAGTAACAATCAGTTTTGCCAATCACACTTCCTGCCGATGCATGTCTAAAACTGGATGTT
     430                        450                        470

TyrArgGlnValHisSerIleIleArgArgSerLeuProAlaThrLeuProGlnCysGln
TACAGACAAGTTCATTCCATTATTAGACGTTCCCTGCCAGCAACACTACCACAGTGTCAG
 490                        510                        530

AlaAlaAsnLysThrCysProThrAsnTyrMetTrpAsnAsnHisIleCysArgCysLeu
GCAGCGAACAAGACCTGCCCCACCAATTACATGTGGAATAATCACATCTGCAGATGCCTG
        550                        570                        590

AlaGlnGluAspPheMetPheSerSerAspAlaGlyAspAspSerThrAspGlyPheHis
GCTCAGGAAGATTTTATGTTTTCCTCGGATGCTGGAGATGACTCAACAGATGGATTCCAT
        610                        630                        650

AspIleCysGlyProAsnLysGluLeuAspGluThrCysGlnCysValCysArgAla
GACATCTGTGGACCAAACAAGGAGCTGGATGAAGAGACCTGTCAGTGTGTCTGCAGAGCG
     670                        690                        710

FIGURE 9B

```
GlyLeuArgProAlaSerCysGlyProHisLysGluLeuAspArgArgAsnSerCysGlnCys
GGGCTTCGGCCTGCCAGCTGTGGACCCCACAAAGAACTAGACAGAAACTCATGCCAGTGT
         730              750              770

ValCysLysAsnLysLeuPheProSerGlnCysGlyAlaAsnArgGluPheAspGluAsn
GTCTGTAAAAACAAACTCTTCCCCAGCCAATGTGGGGCCAACCGAGAATTTGATGAAAAC
         790              810              830

ThrCysGlnCysValCysLysArgThrCysProArgAsnGlnProLeuAsnProGlyLys
ACATGCCAGTGTGTATGTAAAAGAACCTGCCCCAGAAATCAACCCCTAAATCCTGGAAAA
         850              870              890

CysAlaCysGluCysThrGluSerProGlnLysCysLeuLeuLeuLysGlyLysLysPheHis
TGTGCCTGTGAATGTACAGAAAGTCCACAGAAATGCTTGTTAAAGGAAAGAAGTTCCAC
         910              930              950

HisGlnThrCysSerCysTyrArgArgProCysThrAsnArgGlnLysAlaCysGluPro
CACCAAACATGCAGCTGTTACAGACGGCCATGTACGAACCGCCAGAAGGCTTGTGAGCCA
         970              990              1010

GlyPheSerTyrSerGluGluValCysArgCysValProSerTyrTrpLysArgProGln
GGATTTTCATATAGTGAAGAAGTGTGTCGTTGTGTCCCTTCATATTGGAAAAGACCACAA
         1030             1050             1070

MetSerEnd
ATGAGCTAAGATTGTACTGTTTCCAGTTCATCGATTTCTATTATGGAAAACTGTGTTG
         1090             1110             1130
```

FIGURE 9C

```
                                                                    50
PDGF-A   .MRTWACLLL LGCGYLAHAL AEEAEIPREL IERLARSQIH SIRDLQRLLE
PDGF-B   MNRCWA.LFL SLCCYLRLVS AEGDPIPEEL YEMLSDHSIR SFDDLQRLLH
PlGF     .......... .......... .......... ........MP VMRLFPCFLQ LLAGLAL...
VEGF     .......... .......... .......... .......... .MNFLLSWVH WSLALLLYLH
FLT4-L   .......... .......... .......... .......... MTVLYPEYWK MYKCQLRKGG
                                                                   100
PDGF-A   IDSVGAEDAL ETSLRAHGSH AINHVPEKRP VPIRRKRSI. ......EEAIP
PDGF-B   GDP.GEEDGA ELDLNMTRSH SGGELES... .LARGRRSLG SLTIAEPAMI
PlGF     PAVPPQQWAL SA........ .......... GNGSSEVEVV P.FQEVWG.. .........R
VEGF     HAKWSQAAPM AE........ .......... GGGQNHHEVV K.FMDVYQ.. .........R
FLT4-L   WQHNREQANL NSRTEETIKF AAAHYNTEIL KSIDNEWR.. .........K
                                                                   150
PDGF-A   AVCKTRTVIY EIPRSQVDPT SANFLIWPPC VEVKRCTGCC NTSSVKCQPS
PDGF-B   AECKTRTEVF EISRRLIDRT NANFLVWPPC VEVQRCSGCC NNRNVQCRPT
PlGF     SYCRALERLV DVVSEY..PS EVEHMFSPSC VSLLRCTGCC GDENLHCVPV
VEGF     SYCHPIETLV DIFQEY..PD EIEYIFKPSC VPLMRCGGCC NDEGLECVPT
FLT4-L   TQCMPREVCI DVGKEF..GV ATNTFFKPPC VSVYRCGGCC NSEGLQCMNT
                                                                   200
PDGF-A   RVHHRSVKVA KVEYVRKKPK LKEVQVRLEE HLECAC.... AT........
PDGF-B   QVQLRPVQVR KIEIVRKKPI FKKATVTLED HLACKC.... ETVAAARPVT
PlGF     ETANVTMQLL KIRSG..DRP .SYVELTFSQ HVRCECRPLR EKMKPERC..
VEGF     EESNITMQIM RIKPH..QGQ .HIGEMSFLQ HNKCECRPKK DRARQENP..
FLT4-L   STSYLSKTLF EITVPLSQGP .KPVTISFAN HTSCRCMSKL DVYRQVHSII
```

FIGURE 10A

```
PDGF-A   201 ..SNLNPDHR EEETDVR... .......... .......... .......... 250
PDGF-B       RSPGGSQEQR AKTPQTRVTI RTVRVRRPPK GKHRKFKHTH DKTALKETLG
PlGF         .......... GDAVPRR... .......... .......... ..........
VEGF         .......... CGPCSERRKH LFVQDPQTCK CSCKNTDSRC KARQLELNER
FLT4-L       RRSLPATLPQ CQAANKTCPT NYMWNNHICR CLAQEDFMFS SDAGDDSTDG
         251                                                    300

PDGF-A       .......... .......... .......... .......... ..........
PDGF-B       A......... .......... .......... .......... ..........
PlGF         .......... .......... .......... .......... ..........
VEGF         TCRCDKPRR. .......... .......... .......... ..........
FLT4-L       FHDICGPNKE LDEETCQCVC RAGLRPASCG PHKELDRNSC QCVCKNKLFP
         301                                                    350

PDGF-A       .......... .......... .......... .......... ..........
PDGF-B       .......... .......... .......... .......... ..........
PlGF         .......... .......... .......... .......... ..........
VEGF         .......... .......... .......... .......... ..........
FLT4-L       SQCGANREFD ENTCQCVCKR TCPRNQPLNP GKCACECTES PQKCLLKGKK
         351                                              395

PDGF-A       .......... .......... .......... ....
PDGF-B       .......... .......... .......... ....
PlGF         .......... .......... .......... ....
VEGF         .......... .......... .......... ....
FLT4-L       FHHQTCSCYR RPCTNRQKAC EPGFSYSEEV CRCVPSYWKR PQMS
```

FIGURE 10B

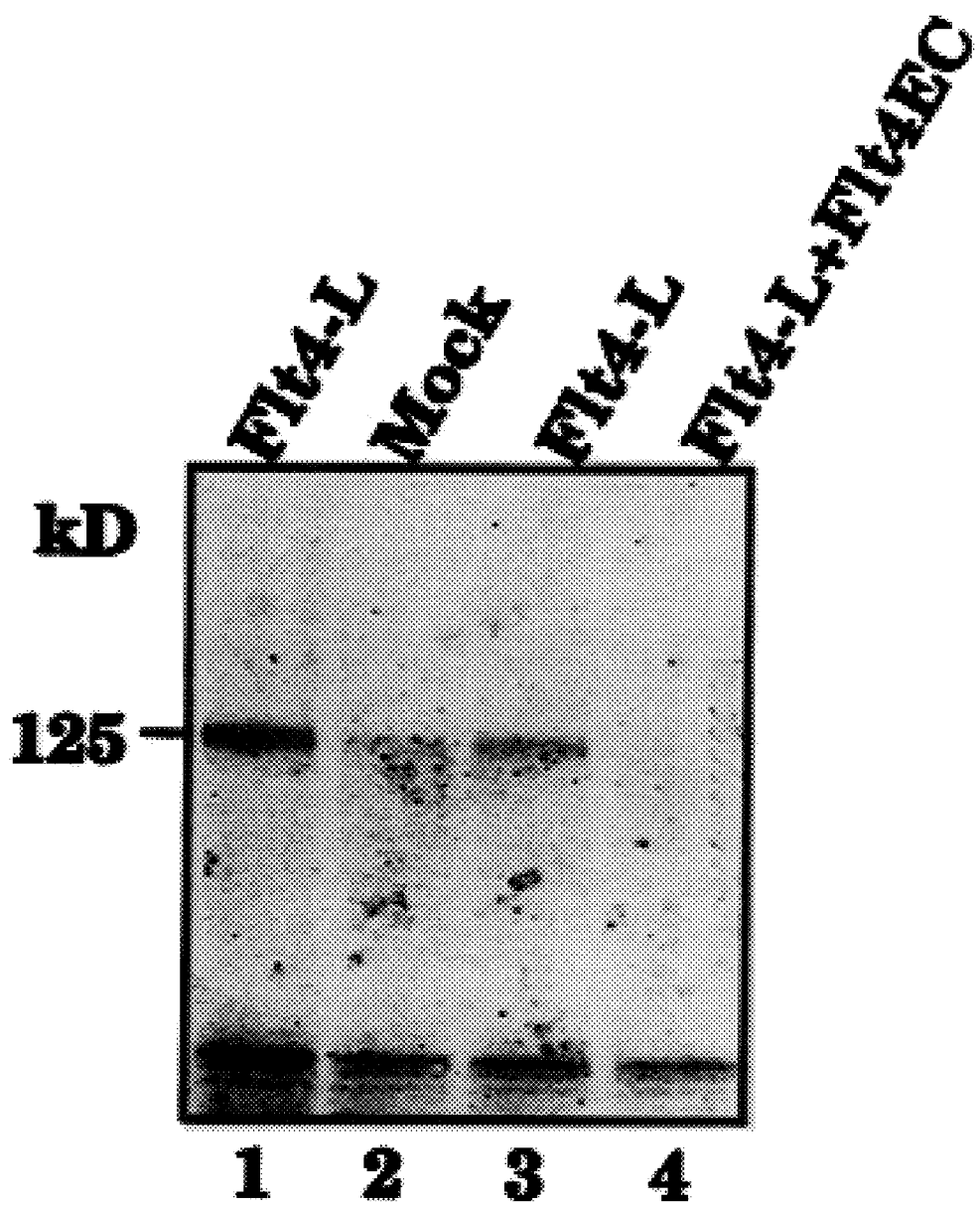
FIGURE II

FIT4 LIGAND AND METHODS OF USE

FIELD OF THE INVENTION

The present invention generally relates to the field of genetic engineering and more particularly to growth factors for endothelial cells and growth factor genes.

BACKGROUND OF THE INVENTION

Developmental growth, the remodelling and regeneration of adult tissues as well as solid tumor growth, can only occur when accompanied by blood vessel formation. Angioblasts and hematopoietic precursor cells differentiate from the mesoderm and form the blood islands of the yolk sac and the primary vascular system of the embryo. The development of blood vessels from these early (in situ) differentiating endothelial cells is termed vasculogenesis. Major embryonic blood vessels are believed to arise via vasculogenesis, whereas the formation of the rest of the vascular tree is thought to occur as a result of vascular sprouting from pre-existing vessels, a process called angiogenesis, Risau, et al., *Devel. Biol.*, 125: 441–450 (1988).

Endothelial cells give rise to several types of functionally and morphologically distinct vessels. When organs differentiate and begin to perform their specific functions, the phenotypic heterogeneity of endothelial cells increases. Upon angiogenic stimulation, endothelial cells may re-enter the cell cycle, migrate, withdraw from the cell cycle and subsequently differentiate again to form new vessels that are functionally adapted to their tissue environment. Endothelial cells undergoing angiogenesis degrade the underlying basement membrane and migrate, forming capillary sprouts that project into the perivascular stroma. Ausprunk, et al., *Microvasc. Rev.*, 14: 51–65 (1977). Angiogenesis during tissue development and regeneration depends on the tightly controlled processes of endothelial cell proliferation, migration, differentiation and survival. Dysfunction of the endothelial cell regulatory system is a key feature of many diseases. Most importantly, tumor growth and metastasis have been shown to be angiogenesis dependent. Folkman, et al., *J. Biol. Chem.*, 267:10931–10934 (1992).

Key signals regulating cell growth and differentiation are mediated by polypeptide growth factors and their transmembrane receptors, many of which are tyrosine kinases. Autophosphorylated peptides within the tyrosine kinase insert and carboxyl-terminal sequences of activated receptors are commonly recognized by kinase substrates involved in signal transduction for the readjustment of gene expression in responding cells. Several families of receptor tyrosine kinases have been characterized. Van der Geer, et al., *Ann. Rev. Cell Biol.*, 10:251–337 (1994). The major growth factors and receptors transducing angiogenic stimuli are schematically shown in FIG. 1.

Fibroblast growth factors are also known to be involved in the regulation of angiogenesis. They have been shown to be mitogenic and chemotactic for cultured endothelial cells. Fibroblast growth factors also stimulate the production of proteases, such as collagenases and plasminogen activators, and induce tube formation by endothelial cells. Saksela, et al., *Ann. Rev. Cell Biol.*, 4:93–126 (1988). There are two general classes of fibroblast growth factors, FGF-1 and FGF-2, both of which lack conventional signal peptides. Both types have an affinity for heparin and FGF-2 is bound to heparin sulfate proteoglycans in the subendothelial extracellular matrix from which it may be released after injury. Heparin potentiates the stimulation of endothelial cell proliferation by angiogenic FGFs, both by protecting against denaturation and degradation and dispersing the FGFs. Cultured endothelial cells express the FGF-1 receptor but no significant levels of other high-affinity fibroblast growth factor receptors.

Among other ligands for receptor tyrosine kinases, the platelet derived growth factor, PDGF-BB, has been shown to be weakly angiogenic in the chick chorioallantoic membrane. Risau, et al., *Growth Factors*, 7:261–266 (1992). Transforming growth factor a (TGFa) is an angiogenic factor secreted by several tumor cell types and by macrophages. Hepatocyte growth factor (HGF), the ligand of the c-met proto-oncogene-encoded receptor, is also strongly angiogenic.

Recent evidence shows that there are endothelial cell specific growth factors and receptors that may be primarily responsible for the stimulation of endothelial cell growth, differentiation and certain differentiated functions. The best studied of these is vascular endothelial growth factor (VEGF), a member of the PDGF family. Vascular endothelial growth factor is a dimeric glycoprotein of disulfide-linked 23 kDa subunits, discovered because of its mitogenic activity toward endothelial cells and its ability to induce vessel permeability (hence its alternative name vascular permeability factor). Other reported effects of VEGF include the mobilization of intracellular calcium, the induction of plasminogen activator and plasminogen activator inhibitor-1 synthesis, stimulation of hexose transport in endothelial cells, and promotion of monocyte migration in vitro. Four VEGF isoforms encoded by distinct mRNA splice variants appear to be equally capable of stimulating mitogenesis in endothelial cells. However, each has a different affinity for cell surface proteoglycans, which behave as low affinity receptors for VEGF. The 121 and 165 amino acid isoforms of VEGF are secreted in a soluble form, whereas the isoforms of 189 and 206 amino acid residues remain cell surface associated and have a strong affinity for heparin.

The pattern of VEGF expression suggests its involvement in the development and maintenance of the normal vascular system and in tumor angiogenesis. During murine development, the entire 7.5 day post-coital (p.c.) endoderm expresses VEGF and the ventricular neuroectoderm produces VEGF at the capillary ingrowth stage. Breier, et al., *Development*, 114:521–523 (1992). On day two of quail development, the vascularized area of the yolk sac as well as the whole embryo show expression of VEGF. In addition, epithelial cells next to fenestrated endothelia in adult mice show persistent VEGF expression, suggesting a role in the maintenance of this specific endothelial phenotype and function.

Two high affinity receptors for VEGF have been characterized. These are VEGFR-1/Flt-1 (fms-like tyrosine kinase-1) and VEGFR-2/Kdr/Flk-1 (kinase insert domain containing receptor/fetal liver kinase-1). Those receptors are classified in the PDGF-receptor family, but they have seven rather than five immunoglobulin-like loops in their extracellular domain and they possess a longer kinase insert than normally observed in this family. The expression of VEGF receptors occurs mainly in vascular endothelial cells, although some may be present on monocytes and melanoma cells. Only endothelial cells have been reported to proliferate in response to VEGF and endothelial cells from different sources show different responses. Thus, the signals mediated through VEGFR-1 and VEGFR-2 appear to be cell type specific.

The Flt4 receptor tyrosine kinase is closely related in structure to the products of the VEGFR-1 and VEGFR-2 genes. Despite this similarity, the mature form of Flt4 differs from the VEGF receptors in that it is proteolytically cleaved in the extracellular domain into two disulfide-linked polypeptides. Pajusola et al., *Cancer Res.*, 52:5738–5743 (1992). The 4.5 and 5.8 kb Flt-4 mRNAs encode polypeptides which differ in their C-termini due to the use of alternative 3' exons. The VEGFs do not show specific binding to Flt4 or induce its autophosphorylation.

Expression of Flt4 appears to be more restricted than expression of VEGFR-1 or VEGFR-2. The expression of Flt4 first becomes detectable by in situ hybridization in the angioblasts of head mesenchyme, the cardinal vein, and extraembryonically in the allantois of 8.5 day p.c. mouse embryos. In 12.5 day p.c. embryos the Flt-4 signal is observed in developing venous and presumptive lymphatic endothelia, but arterial endothelia appear negative. During later stages of development, Flt4 mRNA becomes restricted to developing lymphatic vessels. Only the lymphatic endothelia and some high endothelial venules express Flt4 mRNA in adult human tissues and increased expression occurs in lymphatic sinuses in metastatic lymph nodes and in lymphangioma. These results support the theory of the venous origin of lymphatic vessels.

SUMMARY OF THE INVENTION

The present invention provides a ligand for the Flt4 receptor tyrosine kinase. In a preferred embodiment, the ligand comprises a fragment of the amino acid sequence shown in SEQ ID NO: 33 which specifically binds to the Flt4 receptor tyrosine kinase.

The present invention also provides a precursor of an Flt4 ligand, wherein the precursor comprises the amino acid sequence shown in SEQ ID NO: 33. The precursor is proteolytically cleaved upon expression to produce an approximately 23 kD peptide which is the Flt4 ligand. In a preferred embodiment of the invention, an Flt4 ligand is provided which is the cleavage product of the precursor peptide shown in SEQ ID NO: 33 and which has a molecular weight of approximately 23 kD under reducing conditions. The Flt4 ligand comprises approximately the first 180 amino acids shown in SEQ ID NO: 33.

Also in a preferred embodiment, nucleic acids encoding an Flt4 ligand precursor are presented. Due to the degeneracy of the genetic code, numerous such coding sequences are possible, each having in common the coding of the amino acid sequence shown in SEQ ID NO: 33, or portions thereof. Ligand precursors according to the invention, when expressed in an appropriate host cell, produce, via cleavage, a peptide which binds specifically to the Flt4 receptor tyrosine kinase. The nucleotide sequence encoding the Flt4 ligand is within the nucleotide sequence shown in SEQ ID NO: 32.

The present invention also provides a cell line which produces an Flt4 ligand. The ligand may be purified and isolated directly from the cell culture medium. Also provided are vectors comprising DNA encoding the Flt4 ligand and host cells comprising the vectors. Vectors are capable of expressing the Flt4 ligand under the control of appropriate promoters and other control sequences.

Ligands according to the invention may be labeled with a detectable label and used to identify their corresponding receptors in situ. Antibodies, both monoclonal and polyclonal, may be made against a ligand of the invention according to standard techniques in the art. Such antibodies may be used in diagnostic applications to monitor angiogenesis, vascularization, lymphatic vessels and their disease states, wound healing, or certain hematopoietic or leukemia cells or they may be used to block or activate the Flt4 receptor. Labeled Flt4 ligand and anti-Flt4 ligand antibodies may be used as imaging agents in the detection of lymphatic vessels, high endothelial venules, and Flt4 receptors expressed in histochemical tissue sections. The ligand or antibody may be covalently or non-covalently coupled to a suitable supermagnetic, paramagnetic, electron dense, echogenic, or radioactive agent for imaging. Other, non-radioactive labels, such as biotin and avidin may also be used.

The present invention also provides diagnostic and clinical applications for claimed ligands. In a preferred embodiment, Flt4 ligands or precursors of the invention are used to accelerate angiogenesis e.g. during wound healing or to promote the endothelial functions of lymphatic vessels. Ligands may be applied in any suitable manner using an appropriate pharmaceutically-acceptable vehicle. Ligands may also be used to quantify future metastatic risk by assaying biopsy material for the presence of active receptors or ligands in a binding assay or kit using detectably-labeled ligand. An Flt4 ligand according to the invention may also be used to promote re-growth or permeability of lymphatic vessels in, for example, organ transplant patients. Ligands according to the invention may also be used to treat or prevent inflammation, edema, aplasia of the lymphatic vessels, lymphatic obstruction, elephantiasis, and Milroy's disease. Finally, Flt4 ligands may be used to stimulate lymphocyte production and maturation and to promote or inhibit trafficking of leukocytes between tissues and lymphatic vessels or to affect migration in and out of the thymus.

Inhibitors of the Flt4 ligand may be used to control endothelial cell proliferation and lymphangiomas. For example, such inhibitors may be used to arrest metastatic growth or spread or to control other aspects of endothelial cell expression and growth. Inhibitors include antibodies, antisense oligonucleotides, and peptides which block the Flt4 receptor.

DESCRIPTION OF THE DRAWINGS

FIGS. 9A through 9C show the nucleotide and deduced amino acid sequence of the coding portion of Flt4 ligand cDNA.

FIGS. 10A and 10B show a comparison of the deduced amino acid sequences of PDGF-A, -B, two PlGF isoforms, four VEGF isoforms and Flt4 ligand.

FIG. 11 shows the stimulation of autophosphorylation of the Flt4 receptor by conditioned medium from cells transfected with the Flt4-L expression vector

DETAILED DESCRIPTION OF THE INVENTION

The present invention is directed to novel growth factors which are ligands for the Flt4 receptor tyrosine kinase. Claimed ligands are members of a family of platelet-derived growth factors/vascular endothelial growth factors which promote mitosis and proliferation of vascular endothelial cells and/or mesodermal cells. Ligands recognizing the Flt4 receptor tyrosine kinase were purified from a PC-3 prostatic adenocarcinoma cell line (ATCC CRL1435). When applied to a population of cells expressing the Flt4 receptor, ligands of the invention stimulate autophosphorylation, resulting in receptor activation. The invention also provides inhibitors of the Flt4 receptor, including antibodies directed against the receptor. A ligand according to the invention may be coexpressed as a larger precursor which is cleaved to produce the ligand. A coexpressed region in some cases results from alternative splicing of RNA of the ligand gene. Such a co-expressed region may be a function of the particular expression system used to obtain the ligand. The skilled artisan understands that in recombinant production of proteins, additional sequence may be expressed along with a functional peptide depending upon the particular recombinant construct used to express the protein, and subsequently removed to obtain the desired ligand. In some cases the recombinant ligand can be made lacking certain residues of the endogenous/natural ligand. Moreover, it is well-known in that conservative replacements may be made in a protein which do not alter the function of the protein. Accordingly, it is anticipated that such alterations are within the scope of the claims. It is intended that the precursor sequence shown in SEQ ID NO: 33 is capable of stimulating the Flt4 ligand without any further processing in a manner similar to that in which VEGF stimulates its receptor in its unprocessed form.

The following Examples illustrate preferred embodiments of the invention, wherein the isolation, characterization, and function of Flt4 ligands according to the invention is shown.

EXAMPLE 1

Production of pLTRFlt4l Expression Vector

Figure 2A:
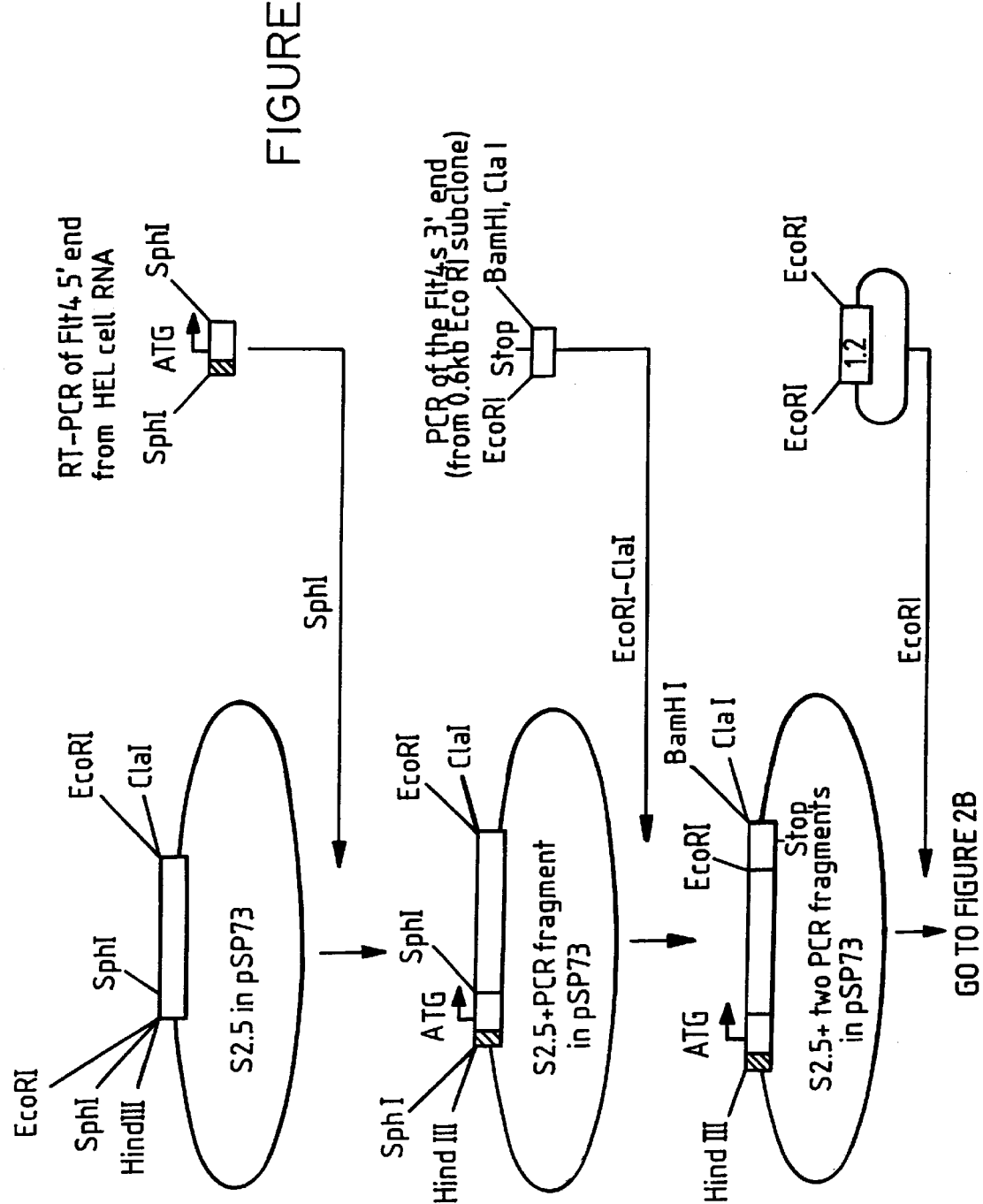
FIGS. 2A and 2B show schematically the construction of the pLTRFlt4l expression vector
Figure 2B:
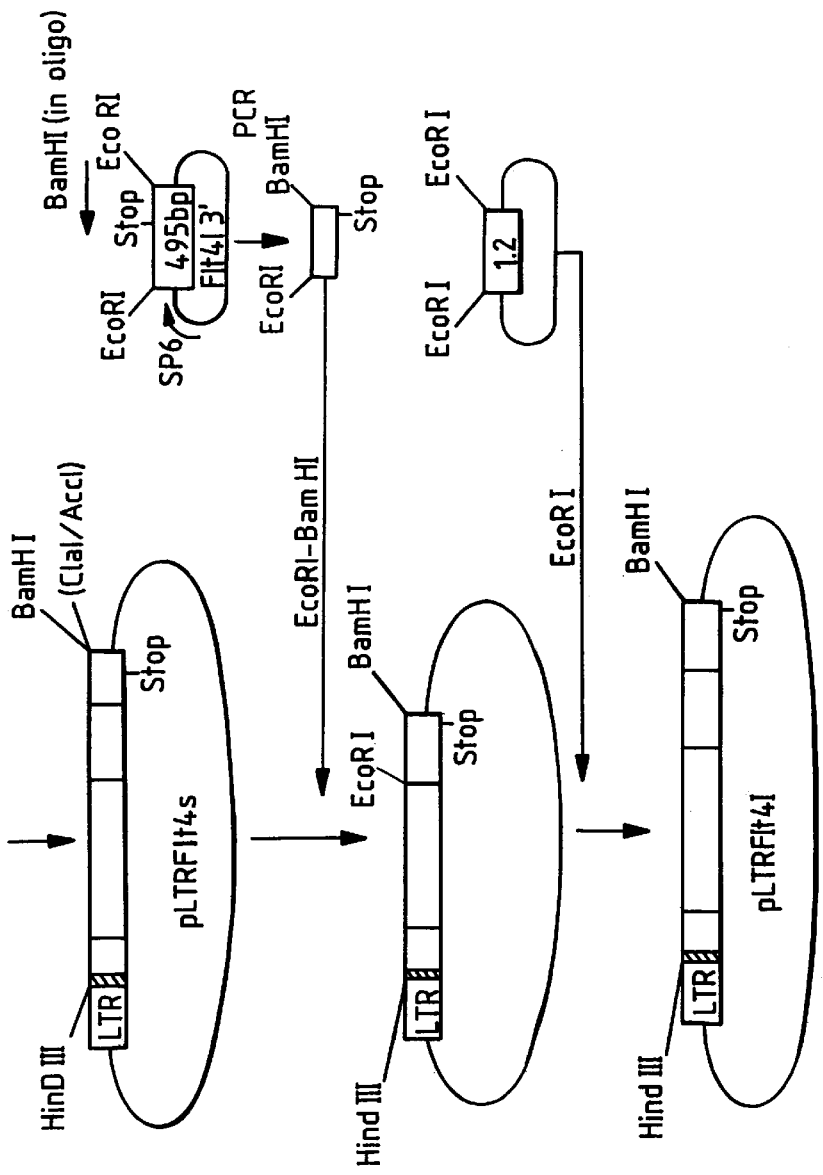

Construction of the LTR-Flt4l vector is schematically shown in FIGS. 2A and 2B. The full-length Flt4s cDNA (Genbank Accession No. X68203) was assembled by first subcloning the S2.5 fragment, reported in Pajusola et al., *Cancer Res.* 52:5738–5743 (1992), incorporated by reference herein, containing base pairs 56–2534 of the Flt4s into the EcoRI site of the pSP73 vector (Promega, Madison, Wis.).

Since cDNA libraries used for screening of Flt4 cDNAs did not contain its most 5' protein-coding sequences, inverse PCR was used for the amplification of the 5' end of Flt4 corresponding to the first 12 amino acid residues (MQRGAALCLRLW). PolyA+RNA was isolated from the HEL cells and double-stranded cDNA copy was synthesized using the Amersham cDNA Synthesis System Plus kit and a gene specific primer: 5'-TGTCCTCGCTGTCCTTGTCT-3' (SEQ ID NO: 1), which was located 195 bp downstream of the 5' end of clone S2.5. Double stranded cDNA was treated with T4 DNA polymerase to blunt the ends and cDNA was purified with Centricon 100 (Amicon Inc., Beverly, Mass.). Circularization was made in a total volume of 150 ul. The reaction mixture contained ligation buffer, 5% PEG-8000, 1 mM DTT and 8 U of T4 DNA ligase (New England Biolabs). Ligation was carried out at 16° C. for 16 hours. Fifteen µl of this reaction mix was used in a standard 100 µl PCR reaction containing 100 ng of specific primers including SacI and PstI restriction sites, present in this segment of the Flt4 cDNA, and 1 unit of Taq DNA polymerase (Perkin Elmer Cetus). Two rounds of PCR were performed using 33 cycles (denaturation at 95° C. for 1 minute, annealing at 55° C. for 2 minutes and elongation at 72° C. for 4 minutes). The PCR mixture was treated sequentially with the SacI and PstI restriction enzymes and after purification with MagicPCR Preps (Promega) DNA fragments were subcloned into the pGEM3Zf(+) vector for sequencing. The sequence obtained corresponds to the 5' end of the Flt4s cDNA clone deposited in the Genbank Database as Accession No. X68203.

Figure 1:
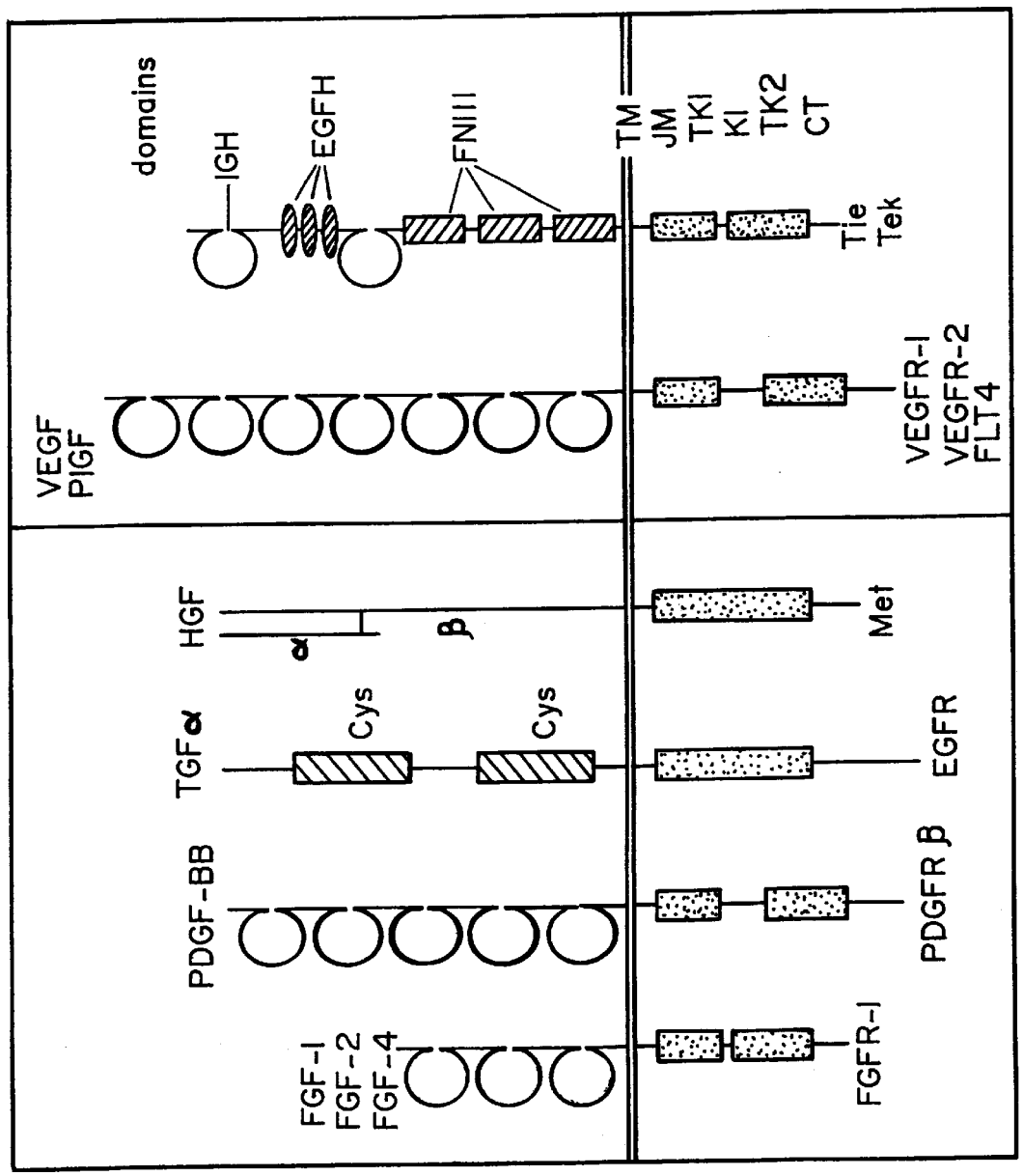
FIG. 1 is a schematic diagram showing major endothelial cell receptor tyrosine kinases and growth factors involved in vasculogenesis and angiogenesis.

The sequence encoding the first 12 amino acid residues was added to the expression construct by ligating an SphI digested PCR fragment amplified using reverse transcription-PCR of polyA+RNA isolated from the HEL cells using the oligonucleotides 5'-ACAT<u>GCATGC</u> CACCATGCAG CGGGGCGCCG CGCTGTGCCT GCGACTGTGG CTCTGCCTGG GACTCCTGGA-3' (SEQ ID NO: 2) (forward primer, SphI site underlined, the translational start codon marked in bold follows an optimized Kozak consensus sequence Kozak, *Nucl. Acids Res.* 15: 8125–8148, 1987) and 5'-ACAT<u>GCATGC</u> CCCGCCGGT CATCC-3' (SEQ ID NO: 3) (reverse primer, SphI site underlined) to the 5' end of the S2.5 fragment, thus replacing unique SphI fragment of the S2.5 plasmid. The resulting vector was digested with EcoRI and ClaI and ligated to a 138 bp PCR fragment amplified from the 0.6 kb EcoRI fragment (base pairs 3789 to 4416 in the Genbank X68203 sequence) which encodes the 3' end of Flt4s shown in FIG. 1 of Pajusola et al., *Cancer Res.* 52:5738–5743, 1992, using the oligonucleotides 5'-CG<u>GAATTC</u>CC CATGACCCCA AC-3' (SEQ ID NO: 4) (forward, EcoRI site underlined) and 5'-CC <u>ATCGAT</u>GG ATCCTACCTG AAGCCGCTTT CTT-3' (SEQ ID NO: 5) (reverse, ClaI site underlined). The coding domain was completed by ligation of the 1.2 kb EcoRI fragment (base pairs 2535–3789 of sequence X68203) into the above construct. The complete cDNA was subcloned as a HindIII-ClaI(blunted) fragment (this ClaI site was also included in the 3' primer used to construct the 3' end of the coding sequence) to the pLTRpoly expression vector reported in Mäkelä et al., *Gene,* 118: 293–294 (1992) (Genbank accession number X60280), incorporated by reference herein, using its HindIII-Acc I(blunted) restriction sites.

The long form of Flt4 was produced by replacing the 3'-end of the short form as follows: The 3' region of the Flt4l cDNA was PCR-amplified using a gene specific and a pGEM 3Z vector specific (SP6 promoter) oligonucleotide 5'-ATTTAGGTGACACTATA-3' (SEQ ID NO: 6) as reverse and forward primers, respectively, and an Flt4l cDNA clone containing a 495 bp EcoRI fragment extending downstream of the EcoRI site at nucleotide 3789 of the Genbank X68203 sequence (the sequence downstream of this EcoRI site is deposited as the Flt4 long form 3' sequence having Genbank accession number S66407). The gene specific oligonucleotide contained a BamHI restriction site located right after the end of the coding region. The sequence of that (reverse primer) oligonucleotide was 5'-CC ATCGAT <u>GGATCCC</u>GATGCTGCTTAGTAGCTGT-3' (SEQ ID NO:

7) (BamHI site is underlined). The PCR product was digested with EcoRI and BamHI and transferred in frame to LTRFlt4s vector fragment from which the coding sequences downstream of the EcoRI site at base pair 2535 (see sequence X68203) had been removed by EcoRI-BamHI digestion. Again, the coding domain was completed by ligation of the 1.2 kb EcoRI fragment (base pairs 2535–3789 of sequence X68203) back into the resulting construct.

EXAMPLE 2

Production and Analysis of Flt4l Transfected Cells

NIH3T3 cells (60% confluent) were cotransfected with 5 μg of the pLTRFlt4l construct and 0.25 μg of the pSV2neo vector (ATCC) containing the neomycin phosphotransferase gene, using the DOTAP liposome-based transfection reagents (Boehringer Mannheim, Mannheim, Germany). One day after the transfection the cells were transferred into selection media containing 0.5 mg/ml geneticin (GIBCO, Grand Island, N.Y.). Colonies of geneticin-resistant cells were isolated and analysed for expression of the Flt4 proteins. Cells were lysed in boiling lysis buffer containing 3.3% SDS (sodium dodecyl sulphate), 125 mM Tris, pH 6.8. Protein concentrations of the samples were measured by the BCA method (Pierce, Rockford, Ill.). About 50 μg protein of each lysate was analysed for the presence of Flt4 by 6% SDS-polyacrylamide gel electrophoresis (SDS-PAGE) and immunoblotting using antisera against the carboxyl terminus of Flt4 and the ECL method (Amersham).

For production of anti-Flt4 antiserum the Flt4 cDNA fragment encoding the 40 carboxyterminal amino acid residues of the short form: NH2-PMTPTTYKG SVDN-QTDSGM VLASEEFEQI ESRHRQESGFR-COOH (SEQ ID NO: 8) was cloned as a 657 bp EcoRI-fragment into the pGEX-11T bacterial expression vector (Pharmacia) in frame with the glutathione-S-transferase coding region. The resulting GST-Flt4S fusion protein was produced in *E. coli* and purified by affinity chromatography using a glutathione-Sepharose 4B column. The purified protein was lyophilized, dissolved in phosphate buffered saline (PBS), mixed with Freund's adjuvant and used for immunization of rabbits at biweekly intervals using methods standard in the art (Harlow and Lane, Antibodies, A Laboratory Manual, Cold Spring Harbor Laboratory Press, 1988). Antisera were used after the fourth booster immunization for immunoprecipitation of Flt4 from the transfected cells and clones expressing Flt4 were used for ligand stimulation analysis.

EXAMPLE 3

Figure 3:
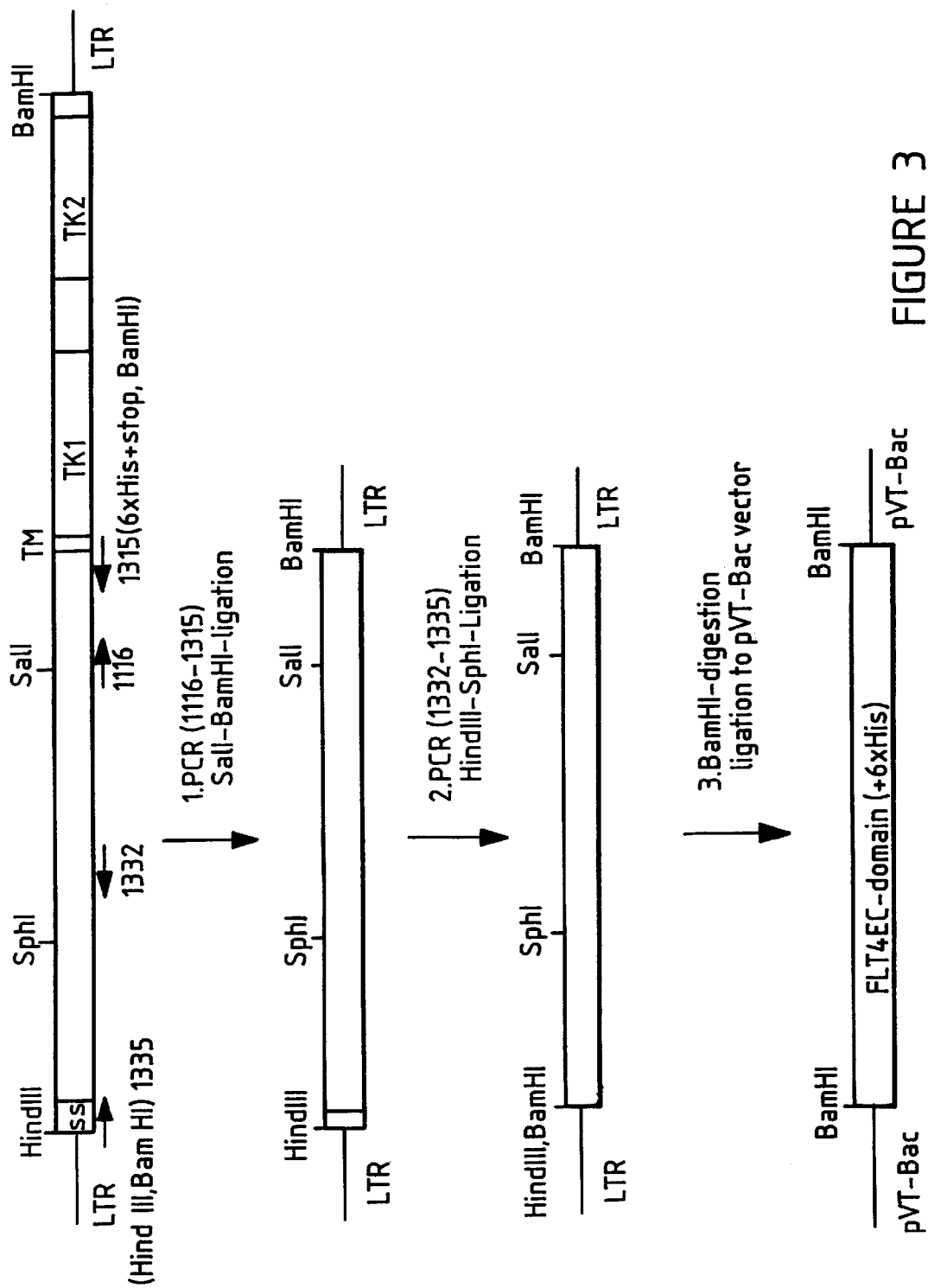
FIG. 3 shows schematically the construction of the baculovirus vector encoding a secreted soluble Flt4EC domain

Construction of a Flt4 EC Baculovirus Vector and Expression and Purification of its Product The construction of an Flt4 extracellular domain (EC) baculovirus vector is schematically shown in FIG. 3. The Flt4-encoding cDNA has been prepared in both a long form and a short form, each being incorporated in a vector under control of the Moloney murine leukemia virus LTR promoter. The nucleotide sequence of the short form of the Flt4 receptor is available on the Genbank database as Accession No. X68203 and the specific 3' segment of the long form cDNA is available as Accession No. S66407.

The ends of a cDNA segment encoding Flt4 extracellular domain (EC) were modified as follows: The 3' end of Flt4 cDNA sequence (Genbank Accession Number X68203) which encodes the extracellular domain was amplified using primer 1116 5'-CTGGA<u>GTCGAC</u>TTGGCGGACT-3' (SEQ ID NO: 9, SalI site underlined) and primer 1315 5'-CGC <u>GGATCC</u>CTAGTGATGGTGATGGTGATGTCTACCTTC GATCATG CTGCCCTTAT CCTC-3' (SEQ ID NO: 10, BamHI site underlined). The sequence complementary to that of primer 1315 continues after the Flt4 reading frame and encodes 6 histidine residues for binding to a Ni-NTA column (Qiagen, Hilden, Germany) followed by a stop codon, and an added Bam HI site. The amplified fragment was digested with SalI and BamHI and used to replace a unique SalI-BamHI fragment in the LTRFlt4 vector shown in FIG. 3. The SalI-BamHI fragment that was replaced encodes the Flt4 transmembrane and cytoplasmic domains.

The 5' end without the Flt4 signal sequence encoding region was amplified by PCR using the primer 1335 5'-CCC <u>AAGCTTGGATCC</u>AAGTGGCTACTCCATGACC-3' (SEQ ID NO: 11) (the primer contains added HindIII (AAGCTT) and BamHI (GGATCC) restriction sites, which are underlined) and primer 1332 5'-GTTGCCTGTGATGTGCACCA-3' (SEQ ID NO: 12). The amplified fragment was digested with HindIIII and SphI (the HindIII site (AAGCTT) is underlined in primer 1335 and the SphI site is within the amplified region of the Flt4l cDNA). The resulting HindIII-SphI fragment was used to replace a HindIII-SphI fragment in the modified LTRFlt4l vector described immediately above (the HindIII site is in the 5' junction of the Flt4 insert with the pLTRpoly portion of the vector, the SphI site is in Flt4 cDNA). The resulting Flt4EC insert was then ligated as a BamHI fragment into the BamHI site in the pVTBac plasmid as disclosed in Tessier et al., Gene 98: 177–183 (1991), incorporated by reference herein. The orientation was confirmed to be correct by partial sequencing so that the open reading frame of the signal sequence-encoding portion of the vector continued in frame with the Flt4 sequence. That construct was transfected together with the baculovirus genomic DNA into SF-9 cells by lipofection. Recombinant virus was purified, amplified and used for infection of High-Five cells (Invitrogen, San Diego, Calif.) using methods standard in the art. The Flt4 extracellular domain was purified from the culture medium of the infected High-Five cells using Ni-NTA affinity chromatography according to manufacturer's instructions (Qiagen) for binding and elution of the 6xHis tag encoded in the COOH-terminus of the recombinant Flt4 extracellular domain.

EXAMPLE 4

Isolation of Flt4 Ligand from Conditioned Media

An Flt4 ligand according to the invention was isolated from conditioned media from PC-3 prostatic adenocarcinoma cell line CRL1435 from the American Type Culture Collection and cultured as instructed by the supplier in Ham's F-12 Nutrient mixture (GIBCO) containing 7% fetal calf serum. In order to prepare the conditioned media, confluent PC-3 cells were cultured for 7 days in Ham's F-12 Nutrient mixture (GIBCO) in the absence of fetal bovine serum. Medium was then cleared by centrifugation at 10,000 g for 20 minutes. The medium was then screened to determine its ability to induce tyrosine phosphorylation of Flt4 by exposure to NIH3T3 cells which had been transfected with Flt4-encoding cDNA using the pLTRFlt4l vector. For receptor stimulation experiments, subconfluent NIH3T3 cells were starved overnight in serum-free DMEM medium (GIBCO) containing 0.2% BSA. The cells were stimulated with the conditioned media for 5 minutes, washed twice with cold PBS containing 100 uM vanadate and lysed in RIPA buffer (10 mM Tris pH 7.5, 50 mM NaCl, 0.5% sodium deoxycholate, 0.5% Nonidet P40 (BDH, Poole, England), 0.1% SDS, 0.1 U/ml Aprotinin (Boehringer Mannheim), 100 uM vanadate) for receptor immunoprecipitation analysis. The lysates were centrifuged for 20 minutes at 15,000×g. The supernatants were incubated for 2 hours on ice with 3 ul of the antiserum against the Flt4 C-terminus described in Example 2 and also in Pajusola, et al. *Oncogene* 8: 2931–2937, (1993), incorporated by reference herein.

After a 2 hour incubation in the presence of anti-Flt4 antiserum, protein A-Sepharose (Pharmacia) was added and incubation was continued for 45 minutes with rotation. The immunoprecipitates were washed three times with the immunoprecipitation buffer and twice with 10 mM Tris, pH7.5 before analysis in SDS-PAGE. Polypeptides were transferred to nitrocellulose and analyzed by Western blotting using Flt4- or phosphotyrosine-specific antisera and the ECL method (Amersham International, Buckinghamshire, England). Anti-phosphotyrosine monoclonal antibodies (anti-PTyr; PY20) were purchased from Transduction Laboratories (Lexington, Ky.). In some cases, the filters were restained with a second antibody after stripping. The stripping of the filters was done for 30 minutes at 50° C. in 100 mM 2-mercaptoethanol, 2% SDS, 62.5 mM Tris-HCl pH 6.7 with occasional agitation.

Figure 4:
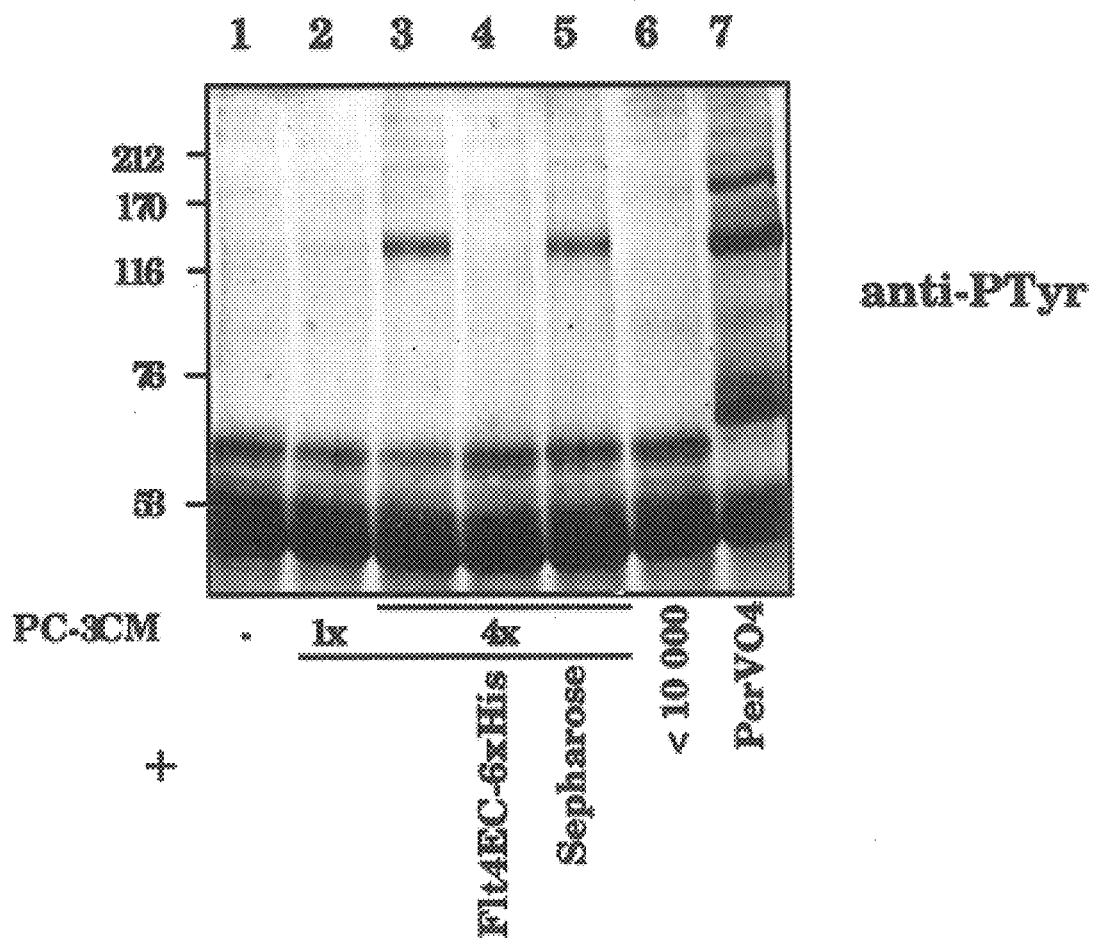
FIG. 4 shows results of stimulation of Flt4 autophosphorylation by conditioned medium from PC-3 cell cultures.
Figures 5A, 5B:
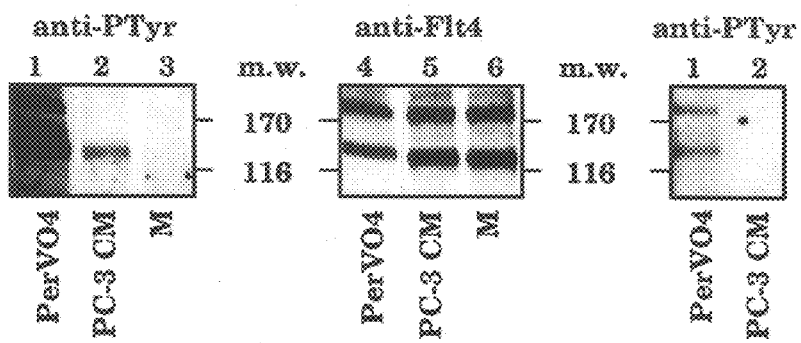
FIGS. 5A–5C show that the tyrosyl phosphorylated polypeptide of Flt4-transfected cells stimulated with PC-3 conditioned medium is the 125 kD Flt4 polypeptide.
Figure 5C:
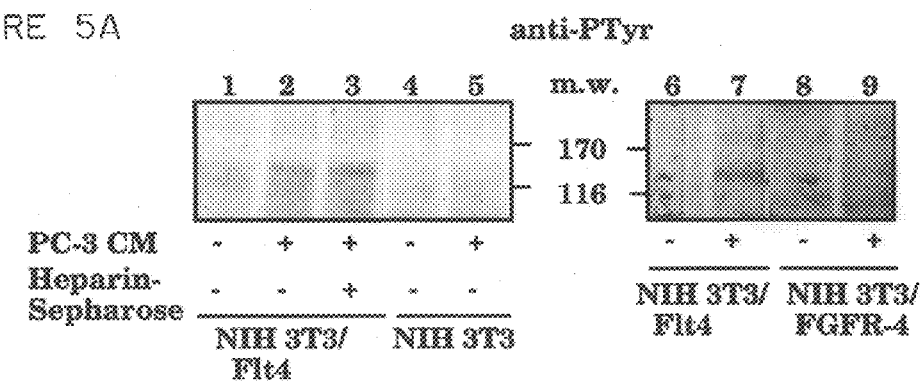

As shown in FIG. 4, the PC-3 cell conditioned medium stimulated tyrosine phosphorylation of a 125 kD polypeptide when Flt4 expressing NIH3T3 cells were treated with the indicated preparations of media, lysed, and the lysates were immunoprecipitated with anti-Flt4 antiserum followed by SDS-PAGE, Western blotting, and staining using anti-PTyr antibodies. The resulting band was weakly phosphorylated upon stimulation with unconcentrated PC-3 conditioned medium (lane 2). The 125 kD band comigrated with the tyrosine phosphorylated, processed form of the mature Flt4 from pervanadate-treated cells (compare lanes 2 and 7 of FIG. 4, see also FIG. 5A). Comigration was confirmed upon restaining with anti-Flt4 antibodies as is also shown in FIG. 5A (panel on the right). In order to show that the 125 kD polypeptide is not a non-specific component of the conditioned medium reactive with anti-phosphotyrosine antibodies, 15 ul of conditioned medium was separated by SDS-PAGE, blotted on nitrocellulose and the blot was stained with anti-PTyr antibodies. No signal was obtained (FIG. 5B). Also, unconditioned medium failed to stimulate Flt4 phosphorylation, as shown in FIG. 4, lane 1.

As shown in FIG. 4, lane 3, stimulating activity was considerably increased when the PC-3 conditioned medium was concentrated four-fold using a Centricon-10 concentrator (Amicon). FIG. 4, lane 4, shows that pretreatment of the concentrated PC-3 conditioned medium with 50 ul of the Flt4 extracellular domain coupled to CNBr-activated sepharose CL-4B (Pharmacia; about 1 mg of Flt4 EC domain/ml sepharose resin) completely abolished Flt4 tyrosine phosphorylation. Similar pretreatment of the conditioned medium with unsubstituted sepharose CL-4B did not affect stimulatory activity, as shown in FIG. 4, lane 5. Also, the flow through obtained after concentration, which contained proteins of less than 10,000 molecular weight, did not stimulate Flt4 phosphorylation, as shown in FIG. 4, lane 6.

The foregoing data show that PC-3 cells produce a ligand which binds to the extracellular domain of Flt4 and activates this receptor.

EXAMPLE 5

Purification of the Flt4 Ligand

The ligand expressed by PC-3 cells as characterized in Example 3 was purified and isolated using a recombinant by produced Flt4 extracellular domain in affinity chromatography.

Two harvests of serum-free conditioned medium, comprising a total of 8 L were collected from 500 confluent 15 cm diameter culture dishes containing confluent layers of PC-3 cells. The conditioned medium was clarified by centrifugation at 10,000×g and concentrated 80-fold using an Ultrasette Tangential Flow Device (Filtron, Northborough, Mass.) with a 10 kD cutoff Omega Ultrafiltration membrane according to the manufacturer's instruction. Recombinant Flt4 extracellular domain was expressed in a recombinant baculovirus cell system and purified by affinity chromatography on Ni-agarose (Ni-NTA affinity column obtained from Qiagen). The purified exracellular domain was coupled to CNBr-activated Sepharose CL-4B at a concentration of 5 mg/ml and used as an affinity matrix for ligand affinity chromatography.

Concentrated conditioned medium was incubated with 2 ml of the recombinant Flt4 extracellular domain-Sepharose affinity matrix in a rolling tube at room temperature for 3 hours. All subsequent purification steps were at +4° C. The affinity matrix was then transferred to a column (Pharmacia) with an inner diameter of 15 mm and washed successively with 100 ml of PBS and 50 ml of 10 mM Na-phosphate buffer (pH 6.8). Bound material was eluted step-wise with 100 mM glycine-HCl, successive 6 ml elutions having pHs of 4.0, 2.4, and 1.9. Several 2 ml fractions of the eluate were collected in tubes containing 0.5 ml 1 M Na-phosphate (pH 8.0). Fractions were mixed immediately and dialysed in 1 mM Tris-HCl (pH 7.5). Aliquots of 75 ul each were analyzed for their ability to stimulate tyrosine phosphorylation of Flt4. The ultrafiltrate, 100 ul aliquots of the concentrated conditioned medium before and after ligand affinity chromatography, as well as 15-fold concentrated fractions of material released from the Flt4 extracellular domain-Sepharose matrix during the washings were also analyzed for their ability to stimulate Flt4 tyrosine phosphorylation.

Figure 6A:
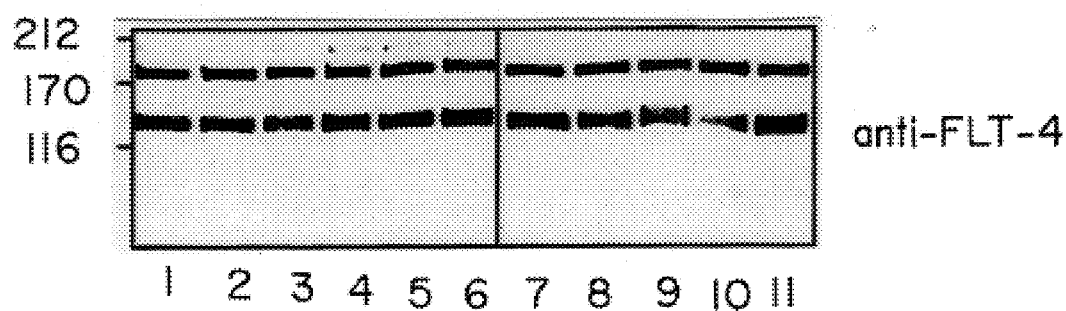
FIGS. 6A and 6B show Western analysis of the Flt4 ligand activity isolated from PC-3 conditioned medium.
Figure 6B:
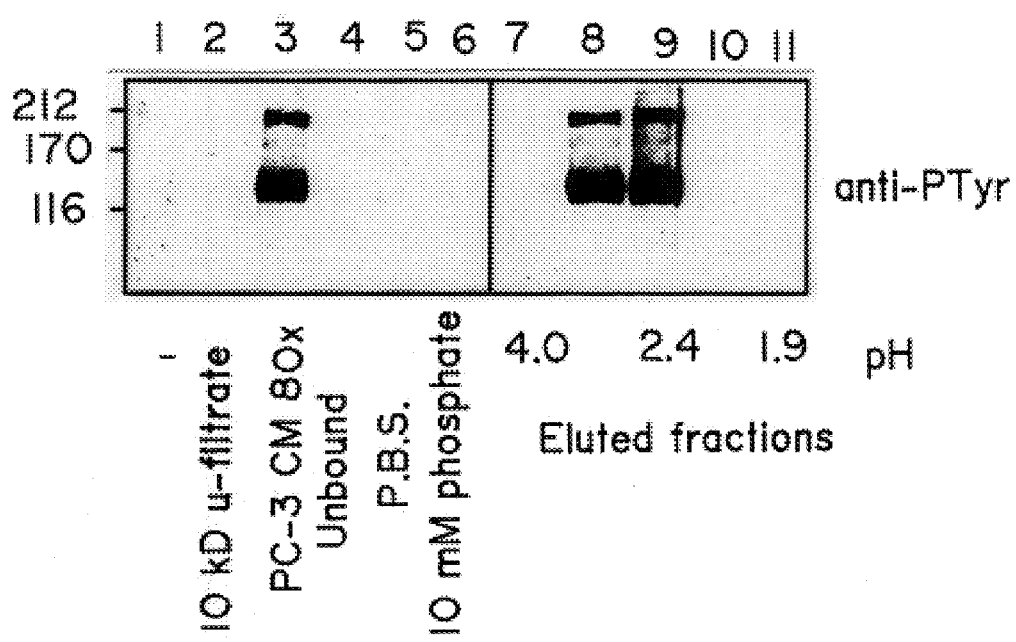

As shown in FIGS. 6A and 6B, lane 3, the concentrated conditioned medium induced prominent tyrosine phosphorylation of Flt4 in transfected NIH3T3 cells overexpressing Flt4. This activity was not observed in conditioned medium taken after medium was exposed to the Flt4 Sepharose affinity matrix described above (lane 4). The specifically-bound Flt4-stimulating material was retained on the affinity matrix upon washes in PBS, 10 mM Na-phosphate buffer (pH 6.8), and at pH 4.0 (lanes 5–7, respectively), and it was eluted in the first two 2 ml aliquots at pH 2.4 (lanes 8 and 9). A further decrease of the pH of the elution buffer did not cause release of additional Flt4-stimulating material (lane 11).

Figure 7:
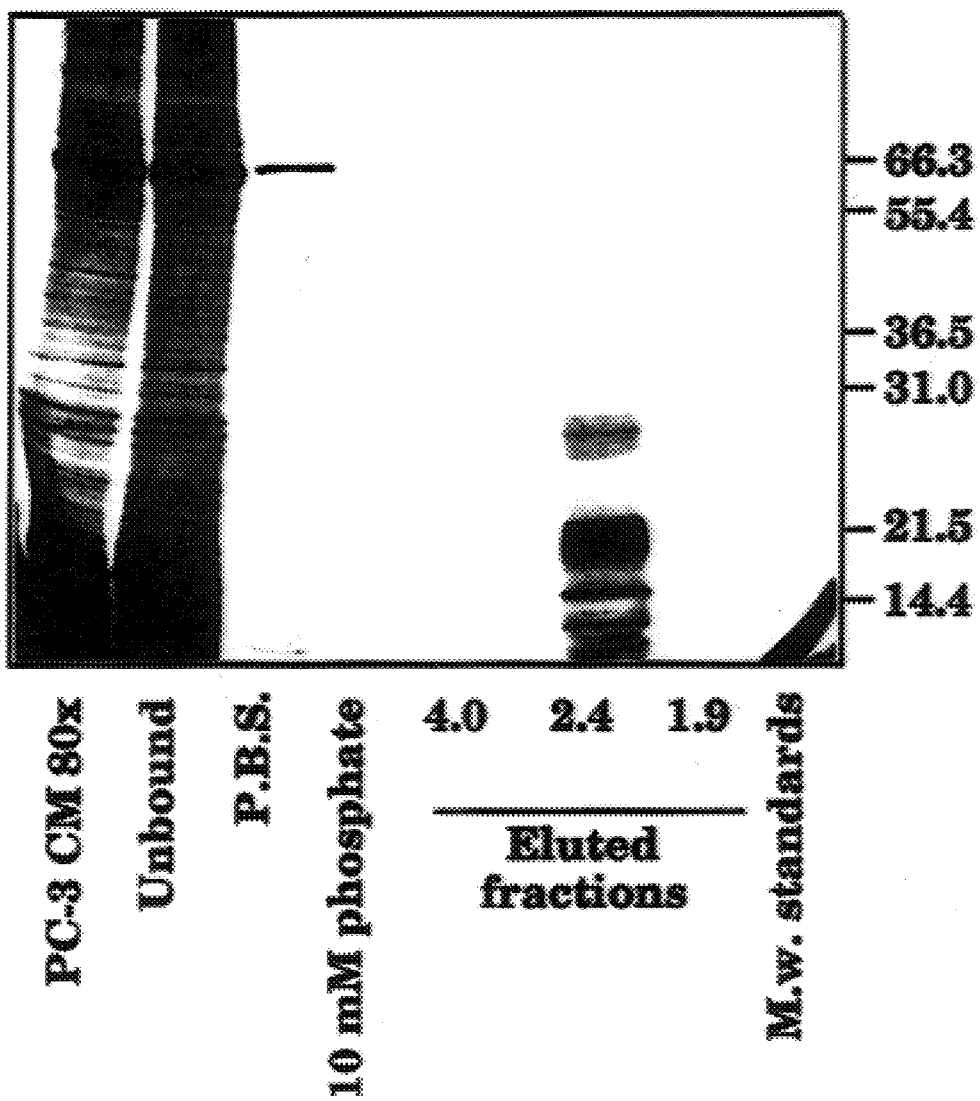
FIG. 7 shows results of gel electrophoresis of fractions from the Western analysis of Flt4 ligand isolated from PC-3 conditioned medium.
Figure 8:
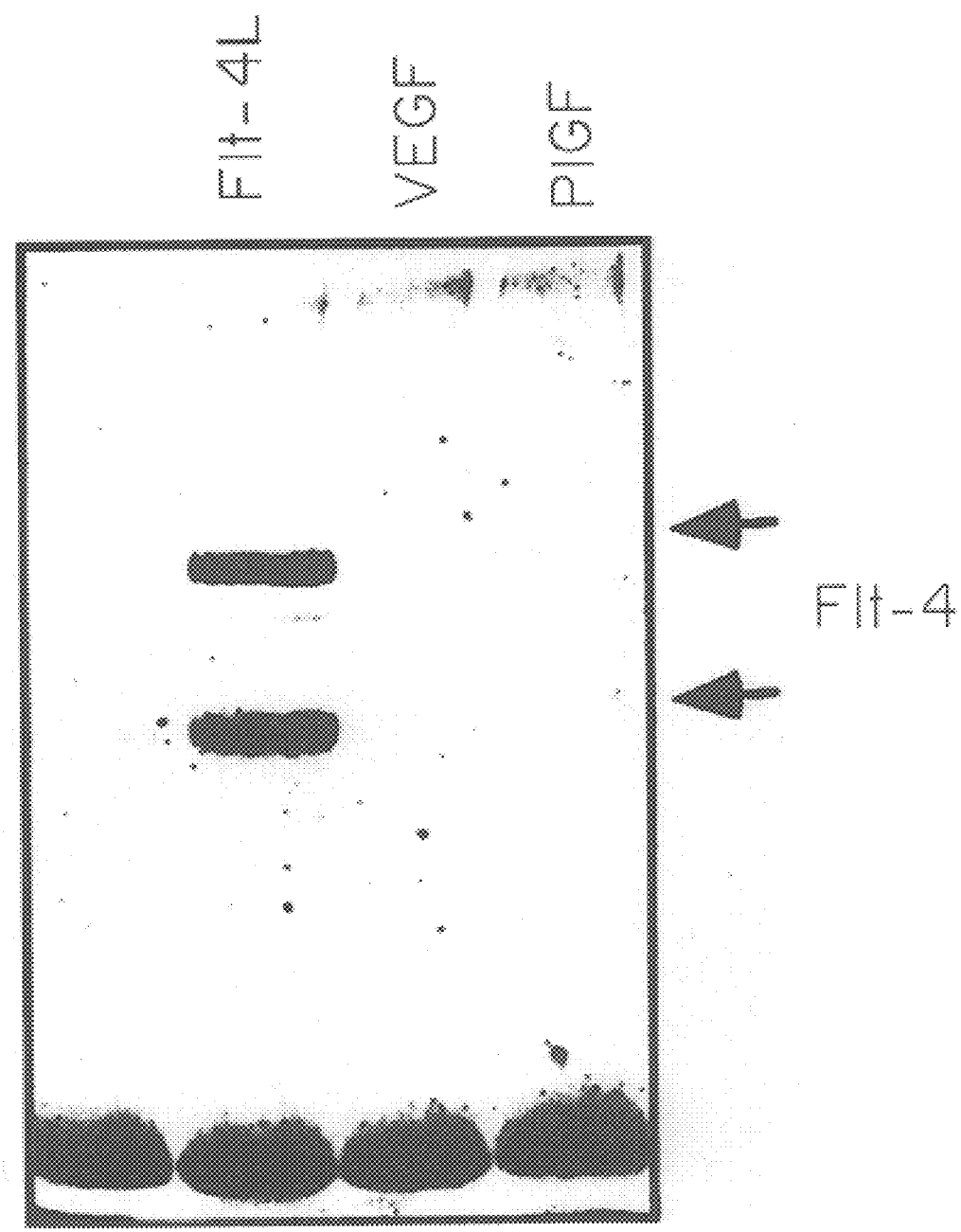
FIG. 8 shows results of Western analysis of Flt4 autophosphorylation induced by either the Flt4 ligand, VEGF, or PlGF.

Small aliquots of the chromatographic fractions were concentrated in a SpeedVac concentrator (Savant, Farmingdale, N.Y.) and subjected to SDS-PAGE under reducing conditions with subsequent silver staining of the gel. As shown in FIG. 7, the major polypeptide, having a molecular weight of approximately 23 kD (reducing conditions), was detected in the fractions containing Flt4 stimulating activity (corresponding to lanes 8 and 9 in FIG. 6). That polypeptide was not found in the other chromatographic fractions. On the other hand, all other components detected in the two active fractions were also distributed in the starting material and in small amounts in the other washing and elution steps after their concentration. Similar results were obtained in three independent affinity purifications, indicating that the 23 kD polypeptide specifically binds to Flt4 and induces its tyrosine phosphorylation.

Fractions containing the 23 kD polypeptide were combined, dried in a SpeedVac concentrator and subjected to SDS-PAGE in a 12.5% gel. The proteins from the gel were then electroblotted to Immobilon-P (PVDF) transfer membrane (Millipore, Malborough, Mass.) and visualized by staining of the blot with Coomassie blue R-250. The region containing only the stained 23 kD band was cut from the blot and was subjected to N-terminal amino acid sequence analysis in a Prosite Protein Sequencing System (Applied Biosystems, Foster City, Calif.). The data were analyzed using a 610A Data Analysis System (Applied Biosystems). Analysis revealed a single N-terminal sequence of $NH_2$-XEETIKFAAAHYNTEILK-COOH (SEQ ID NO: 13).

EXAMPLE 6

Construction of PC-3 Cell cDNA Library in a Eukaryotic Expression Vector

Poly-A+RNA was isolated from five 15 cm diameter confluent dishes of PC-3 cells by a single step method using oligo(dT) (Type III, Collaborative Research) cellulose affinity chromatography (Sambrook et al., Molecular Cloning, A Laboratory Manual; Cold Spring Harbor Laboratory Press, 1989). The yield was 70 µg. Six ug of the poly-A+RNA was used to prepare an oligo(dT)-primed cDNA library in the mammalian expression vector pcDNA I and the Librarian kit of Invitrogen according to the instructions included in the kit. The library was estimated to contain about $10^6$ independent recombinants with an average insert size of approximately 1.8 kb.

EXAMPLE 7

Amplification of the Unique Nucleotide Sequence Encoding the Flt4 Ligand

Degenerate oligonucleotides were designed based on the N-terminal amino acid sequence of the isolated Flt4 ligand and were used as primers in a polymerase chain reaction (PCR) to amplify cDNA encoding the Flt4 ligand from a PC-3 cell library.

The PCR was carried out using 1 µg of DNA from the amplified PC-3 cDNA library and a mixture of sense-strand primers comprising 5'-GCAGARGARACNATHAA-3' (SEQ ID NO: 14) (wherein R is A or G, N is A,G,C or T and H is A, C or T), encoding amino acid residues 2–6 (EETIK, SEQ ID NO: 15) and antisense-strand primers 5'-GCAYTTNARDATYTCNGT-3' (SEQ ID NO: 16) (wherein Y is C or T and D is A, G or T), corresponding to amino acid residues 14–18 (TEILK, SEQ ID NO: 17). Three extra nucleotides (GCA) were added to the 5'-terminus of each primer to increase annealing stability. Two successive PCR runs were carried out using 1 U per reaction of DynaZyme, a thermostable DNA polymerase (F-500L, Finnzymes), in a buffer supplied by the manufacturer (10 mM Tris-HCl, pH 8.8 at 25° C., 1.5 mM $MgCl_2$, 50 mM KCl, 0.1% Triton-X100) at an extension temperature of 72° C. The first PCR run was carried out for 43 cycles. The first three cycles were run at annealing temperature 33° C. for 2 minutes and the remaining cycles were run at 42° C. for 1 minute.

The region of the gel containing a weak band of the expected size (57 bp) was cut out from the gel and eluted. The eluted material was reamplified for 30 cycles using the same primer pairs described above at 42° C. for 1 minute. The amplified fragment was cloned into a pCR II vector (Invitrogen) using the TA cloning kit (Invitrogen) and sequenced using the radioactive dideoxynucleotide sequencing method of Sanger. Six clones were analysed and all contained the sequence encoding the expected peptide (amino acids 2–18 of the Flt4 ligand precursor). Nucleotide sequence spanning the region from the third nucleotide of codon 6 to the third nucleotide of codon 13 (the extension region) was identical in all six clones: 5'-ATTCGCTGCAGCACACTACAAC-3' (SEQ ID NO: 18) and thus was considered to represent an amplified product from the unique sequence encoding part of the amino terminus of the Flt4 ligand.

EXAMPLE 8

Amplification of the 5'-end of the cDNA Encoding the Flt4 Ligand

Based on the unique nucleotide sequence encoding the N-terminus of the isolated Flt4 ligand, two pairs of nested primers were designed to amplify in two subsequent PCR-reactions the complete 5'-end of the corresponding cDNAs from 1 µg of DNA from the above-described PC-3 cDNA library. First, amplification was performed with primer 5'-TCNGTGTTGTAGTGTGCTG-3' (SEQ ID NO: 19) which is the antisense-strand primer corresponding to amino acid residues 9–15 (AAHYNTE, SEQ ID NO: 20) and sense-strand primer 5'-TAATACGACTCACTATAGGG-3' (SEQ ID NO: 21) corresponding to the T7 RNA promoter of the pcDNAI vector used for construction of the library. "Touchdown" PCR was used as disclosed in Don, et al., Nucl. Acids Res., 19: 4008 (1991), incorporated by reference herein. The annealing temperature of the two first cycles was 62° C. and subsequently the annealing temperature was decreased in every other cycle by 1° C. until a final temperature of 53° C. was reached, at which temperature 16 additional cycles were carried out. Annealing time as 1 minute and extension at each cycle was conducted at 72° C. for 1 minute. Multiple amplified DNA fragments were obtained in the first reaction. The products of the first amplification (1 ul of a 1:100 dilution in water) were used in the second amplification reaction employing the nested primers 5'-GTTGTAGTGTGCTGCAGCGAATTT-3' (SEQ ID NO: 22), an antisense-strand primer corresponding to amino acid residues 6–13 (KFAAAHYN, SEQ ID NO: 23) of the Flt4 ligand and 5'-TCACTATAGGGAGACCCAAGC-3' (SEQ ID NO: 24), a sense-strand primer corresponding to nucleotides 2179–2199 of the pcDNAI vector. The sequences of these sense and antisense primers overlapped with the 3' ends of the corresponding primers used in the first PCR. "Touchdown" PCR was carried out by decreasing the annealing temperature from 72° C. to 66° C. and continuing with 18 additional cycles at 66° C. The annealing time was 1 minute and extension at each cycle was carried out at 72° C. for 2 minutes. One major product of about 220 bp and three minor products of about 270 bp, 150 bp, and 100 bp were obtained.

The amplified fragment of approximately 220 bp was cut out from the agarose gel, cloned into a pCRII vector using the TA cloning kit (Invitrogen) and sequenced. Three recombinant clones were analysed and they contained the sequence
5'-TCACTATAGGGAGACCCAAGCTTGGTACCGAGCT CGGATCCACTA GTAACGGCCGCCAGTGTGGTG- GAATTC<u>GACGAACTCATGACTGTA</u>
CTCTACCCAGAATATTGGAAAATGTACAAGTGTCAG CTAAGGCAA
GGAGGCTGGCAACATAACAGAGAACAGGCCAACC TCAACTCAAG
GACAGAAGAGACTATAAAATTCGCTGCAGCACACT ACAAC-3' (SEQ ID NO: 25). The beginning of the sequence represents the pcDNAI vector and the underlined sequence represents the amplified product of the 5'-end of the insert. The ATG codon located upstream of that sequence in the same reading frame is followed by an open reading frame containing the amplified product of the putative signal sequence and the first 13 amino acid residues of the secreted Flt4 ligand.

EXAMPLE 9

Amplification of the 3'-end of cDNA Encoding the Flt4 Ligand

Based upon the amplified 5'-sequence of the clones encoding the Flt4 ligand, two pairs of non-overlapping nested primers were designed to amplify the 3'-portion of the clones. The sense-strand primer 5'-ACAGAGAACAGGCCAACC-3' (SEQ ID NO: 26) and antisense-strand primer 5'-TCTAGCATTTAGGTGACAC-3' (SEQ ID NO: 27) corresponding to nucleotides 2311–2329 of the pcDNAI vector were used in a first "touchdown" PCR. The annealing temperature of the reaction was decreased 1° C. every two cycles from 72° C. to 52° C., at which temperature 15 additional cycles were carried out. The annealing time was 1 minute and extension at each cycle was carried out at 72° C. for 3 minutes. DNA fragments of several sizes were obtained in the first amplification. Those products were diluted 1:200 in water and reamplified in PCR using the second pair of primers: 5'-AAGAGACTATAAAATTCGCTGCAGC-3' (SEQ ID NO: 28) and 5'-CCCTCTAGATGCATGCTCGA-3' (SEQ ID NO: 29) (antisense-strand primer corresponding to nucleotides 2279–2298 of the pcDNAI vector). Two DNA fragments were obtained, having sizes of 1350 bp and 570 bp. Those fragments were cloned into a pCRII vector and the inserts of the clones were sequenced. Both of these fragments were found to contain sequences encoding an amino acid sequence homologous to the VEGF sequence.

EXAMPLE 10

Screening the PC-3 Cell cDNA Library using the 5' PCR Fragment of Flt4 Ligand cDNA A 219 bp 5'-terminal fragment of Flt4 ligand cDNA was amplified by PCR using the 5' PCR fragment described above and primers 5'-GTTGTAGTGTGCTGCAGCGAATTT-3' (antisense-strand primer, SEQ ID NO: 30) and 5'-TCACTATAGGGAGACCCAAGC-3' (SEQ ID NO: 31) (sense-primer corresponding to nucleotides 2179–2199 of the pcDNAI vector). The amplified product was subjected to digestion with EcoRI (Boehringer Mannheim) to remove the portion of the DNA sequence amplified from the pcDNAI vector and the resulting 153 bp fragment encoding the 5' end of the Flt4 ligand was labeled with [$^{32}$P]-dCTP using the Klenow fragment of E. coli DNA polymerase I (Boehringer Mannheim). That fragment was used as a probe for hybridization screening of the amplified PC-3 cell cDNA library.

Filter replicas of the library were hybridized with the radioactively labeled probe at 42° C. for 20 hours in a solution containing 50% formamide, 5×SSPE, 5×Denhardt's solution, 0.1% SDS and 0.1 mg/ml denatured salmon sperm DNA. Filters were washed twice in 1×SSC, 0.1% SDS for 30 minutes at room temperature, then twice for 30 minutes at 65° C. and exposed overnight.

On the basis of autoradiography, 10 positive recombinant bacterial colonies hybridizing with the probe were chosen from the library. Plasmid DNA was purified from these colonies and analysed by EcoRI and NotI digestion and agarose gel electrophoresis followed by ethidium bromide staining. The ten plasmid clones were divided into three groups on the basis of the presence of insert sizes of approximately 1.7, 1.9 and 2.1 kb, respectively. Inserts of plasmids from each group were sequenced using the T7 oligonucleotide as a primer and walking primers for subsequent sequencing reactions.

Sequence analysis showed that all clones contain the open reading frame encoding the NH2-terminal sequence of the Flt4 ligand. Furthermore, the 2.1 and 1.9 kb clones also contained sequences encoding the signal sequence. The 5' end of the 1.7 kb clone began within the signal sequence-encoding portion. Dideoxy sequencing was continued using walking primers in the downstream direction. An 1140 nucleotide portion of the sequence of the longest clone is shown in FIGS. 9A through 9C (SEQ ID NOS: 32 and 33). As can be seen in that figure, after the putative signal sequence the open reading frame terminates in a TAA stop codon 317 amino acid residues further downstream from the signal sequence. When compared with sequences in the GenBank Database, the predicted protein product of this reading frame was found to be homologous with the predicted amino acid sequences of the PDGF/VEGF family of growth factors, as shown in FIGS. 10A and 10B.

EXAMPLE 11

Stimulation of Flt4 Autophosphorylation by the Protein Product of the Flt4 Ligand Vector The 2.1 kb insert of the Flt4-L clone in pcDNAI vector containing the open reading frame encoding the sequence shown in FIGS. 9A through 9C (SEQ ID NO: 32) was cut out from the vector using HindIII and NotI restriction enzymes, isolated from a preparative agarose gel and ligated to the corresponding sites in the pREP7 expression vector (Invitrogen). The pREP7 vector containing the above cloned insert was transfected into 293-EBNA cells (Invitrogen) using the calcium phosphate transfection method (Sambrook et al., Molecular Cloning, A Laboratory Manual; Cold Spring Harbor Laboratory Press, 1989). About 48 hours after transfection the medium of the transfected cells was changed to DMEM medium lacking fetal calf serum and incubated for 36 h. The thus conditioned medium was then collected, centrifuged at 5000×g for 20 minutes, the supernatant was concentrated 5-fold using Centriprep 10 (Amicon) stimulate NIH3T3 cells expressing LTRFlt41, as in Example 4. The cells were lysed, immunoprecipitated using anti-Flt4 antiserum and analysed by Western blotting using anti-phosphotyrosine antibodies.

As can be seen from FIG. 11, lanes 1 and 3, the conditioned medium from two different dishes of the transfected cells stimulated Flt4 autophosphorylation in comparison with the medium from mock-transfected cells, which gave only background levels of phosphorylation of the Flt4 receptor (lane 2). When the concentrated conditioned medium was preabsorbed with 20 µl of a slur of Flt4EC domain coupled to Sepharose (see example 4), no phosphorylation was obtained (lane 4), showing that the activity responsible for Flt4 autophosphorylation was indeed the Flt4 ligand. Thus, these results demonstrate that the Flt4-L plasmid vector clone having an approximately 2.1 kb insert and containing the open reading frame shown in FIGS. 9A through 9C is expressed into a Flt4 ligand in cells transfected with the Flt4-L expression vector clone, and thus is biologically active. The sequence encoded by that open reading frame is shown in SEQ ID NO: 33. Plasmid pFLt4-L has been deposited with the American Type Culture Collection, 12301 Parklawn Drive, Rockville, Md. 20852 as accession number 97231. A 1997 base pair nucleotide sequence and the deduced amino acid sequence of the cDNA insert of this deposited plasmid is set forth in SEQ ID NOS: 34 and 35, respectively.

However, the predicted molecular weight of the mature protein product deduced from this reading frame is 35,724 and the Flt4 ligand from PC-3 cell cultures had an approximate molecular weight of 23 kD under reducing conditions. It is thus possible that the Flt4 mRNA may be first translated into a precursor, from which the mature ligand is derived by proteolytic cleavage. The difference in the observed molecular weight of the isolated Flt4 ligand and the deduced molecular weight of the disclosed open reading frame of the Flt4 ligand sequence may then derive from sequences in the carboxyl terminal region of the latter. Also, the Flt4 ligand may be glycosylated at two putative N-linked glycosylation sites conforming to the consensus which can be identified in the deduced Flt4 ligand amino acid sequence (N-residues underlined in FIG. 10A).

The carboxyl terminal amino acid sequences, which increase the predicted molecular weight of the Flt4 ligand subunit in comparison with other ligands of this family show a pattern of spacing of cysteine residues reminiscent of the Balbiani ring protein 3 (BRP3) sequence (Dignam and Case, Gene 88, 133–140, 1990). Such a sequence may encode an independently folded domain present in a Flt4 ligand precursor and it may be involved, for example, in the regulation of secretion, solubility, stability, cell surface localization or activity of the Flt4 ligand. Interestingly, at least one cysteine motif of the BRP3 type is also found in the VEGF carboxy terminal amino acid sequences.

Thus, the Flt4 mRNA may be first translated into a precursor from the mRNA corresponding to the Flt4-L clone, from which the mature ligand is derived by proteolytic cleavage. To define the mature Flt4 ligand product one first expresses the cDNA clone, which is deposited in the pcDNAI expression vector, in cells, such as COS cells and use antibodies generated against Flt4-L-encoded peptides, such as amino terminal 23 amino acid peptide or bacterial Flt4 fusion proteins, such as a GST-fusion protein, to raise antibodies against the VEGF-homologous domain of Flt4 ligand. One then follows the biosynthesis and processing of the Flt4 ligand in the transfected cells by pulse-chase analysis using radioactive cysteine for labelling of the cells, immunoprecipitation and gel electrophoresis. Using antibodies against the two domains of the product of the Flt4-L clone material for radioactive or nonradioactive aminoterminal sequence analysis is isolated. The determination of the NH2-terminal sequence of the carboxyl terminal fragment allows for identification of the proteolytic processing site. This is confirmed by site-directed mutagenesis of the amino acid residues adjacent to the cleavage site, which would prevent the cleavage.

On the other hand, the Flt4 ligand is characterized by progressive 3' deletions in the 3' coding sequences of the Flt4 ligand precursor clone, resulting in carboxy-terminal truncations of its protein product. The activities of such truncated forms are asaysed by, for example, studying Flt4 autophosphorylation induced by the truncated proteins when applied to cultures of cells, such as NIH3T3 cells expressing LTRFlt4. By extrapolation from studies of the structure of the related platelet derived growth factor (PDGF, reference Heldin et al., Growth Factors 8, 245–252, 1993) one determines that the region critical for receptor activation by the Flt4 ligand is contained within its first approximately 180 amino acid residues.

On the other hand, the difference between the molecular weights of the purified ligand and the open reading frame of the Flt4 precursor clone may be due to the fact that the soluble ligand was produced from an alternatively spliced mRNA which would also be present in the PC-3 cells, from which the isolated ligand was derived. To isolate such alternative cDNA clones one uses cDNA fragments of the deposited clone and PCR primers made according to the sequence provided as well as techniques standard in the art to isolate or amplify alternative cDNAs from the PC-3 cell cDNA library. One may also amplify using reverse transcription (RT)-PCR directly from the PC-3 mRNA using the primers provided in the sequence of the Flt4-L clone. Alternative cDNAs can be sequenced from the resulting cDNA clones. One can also isolate genomic clones corresponding to the Flt4-L transcript from a human genomic DNA library using methods standard in the art and to sequence such clones or their subcloned fragments to reveal the corresponding exons. Alternative exons can then be identified by a number of methods standard in the art, such as heteroduplex analysis of cDNA and genomic DNA and they can subsequently be characterized.

EXAMPLE 12

Expression of the Flt4-L Gene

Figure 12:
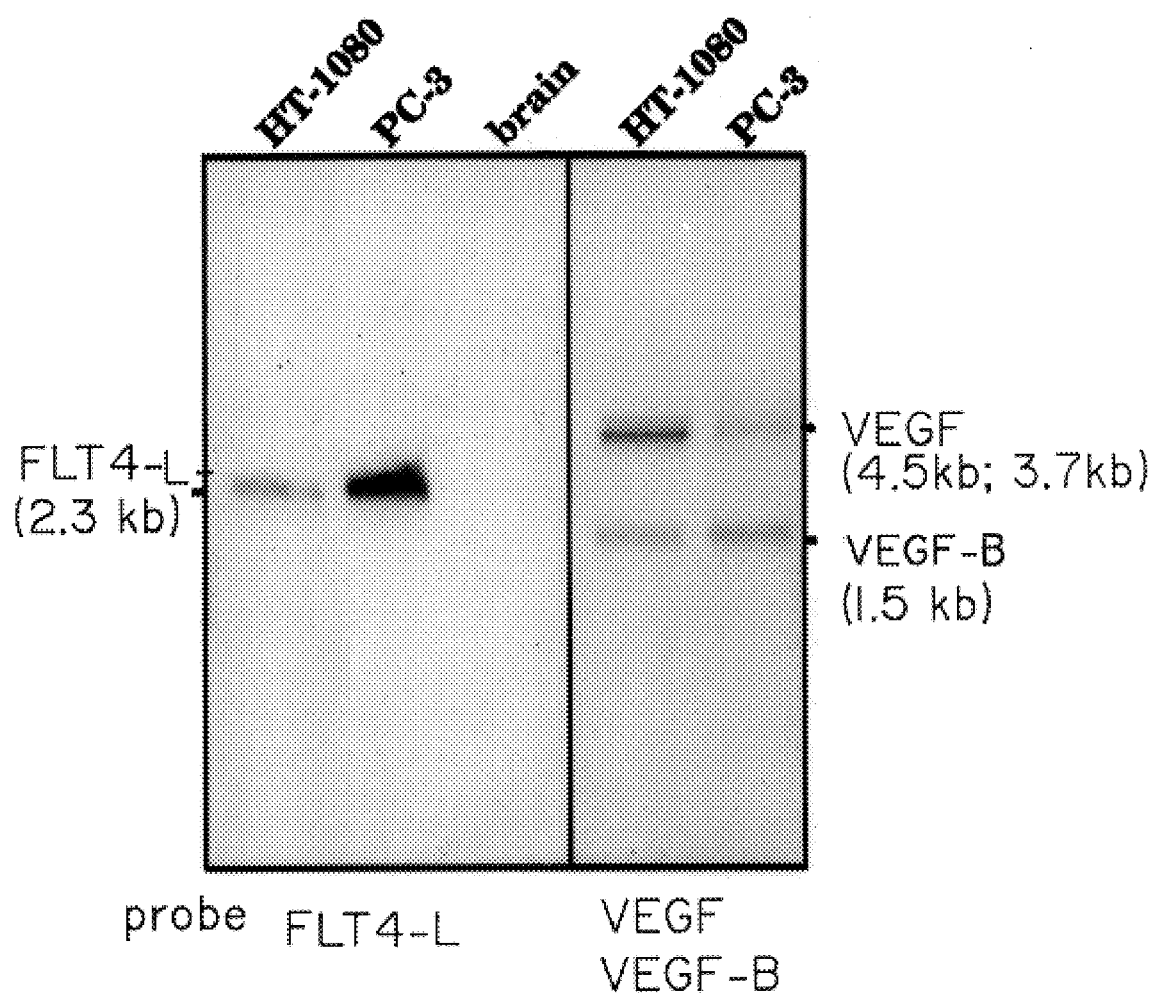
FIG. 12 shows Northern blotting analysis of Flt4-L mRNA in tumor cell lines.

Expression of transcripts corresponding to the Flt4 ligand was analysed by hybridization of Northern blots containing isolated polyA+RNA from HT-1080 and PC-3 human tumor cell lines. The probe was the radioactively labelled insert of the 2.1 kb cDNA clone (specific activity $10^8$–$10^9$ cpm/mg of DNA). The blot was hybridized overnight at 42° C. or using 50% formamide, 5×SSPE buffer, 2% SDS, 10×Denhardts solution, 100 mg/ml salmon sperm DNA and 1×$10^6$ cpm of the labelled probe/ml. The blot was washed at room temperature for 2×30 minutes in 2×SSC containing 0.05% SDS and then for 2×20 min at 52° C. in 0.1×SSC containing 0.1% SDS. The blot was then exposed at −70° C. for three days using intensifying screens and Kodak XAR film. Both cell lines expressed an Flt4 ligand mRNA of about 2.3 kb, as well as VEGF and VEGF-B mRNA:s (FIG. 12).

What is claimed is:

1. A purified and isolated polypeptide capable of binding to an Flt4 receptor tyrosine kinase, said polypeptide comprising a portion of amino acids 1–180 of SEQ ID NO: 33 effective to permit such binding, said polypeptide lacking all of amino acids of SEQ ID NO: 33 beyond position 180.

2. A pharmaceutical composition comprising a polypeptide according to claim 1 in a pharmaceutically-acceptable diluent, adjuvant, or carrier.

3. A method of modulating the activity of human Flt4 receptor tyrosine kinase comprising administering to a person in need of modulation of Flt4 receptor tyrosine kinase activity a composition according to claim 2.

4. A polypeptide according to claim 1 further comprising a detectable label.

5. A purified and isolated polypeptide according to claim 1 that binds Flt4 and stimulates Flt4 phosphorylation in mammalian cells expressing Flt4.

6. A method of modulating the activity of human Flt4 receptor tyrosine kinase comprising contacting cells that express human Flt4 receptor tyrosine kinase with a polypeptide according to claim 1.

7. A purified and isolated polypeptide capable of binding with high affinity to the extracellular domain of Flt4 receptor tyrosine kinase (Flt4), wherein the polypeptide comprises a portion of SEQ ID NO: 33 effective to permit such binding, and wherein the polypeptide has an apparent molecular weight of approximately 23 kD as assessed by SDS-PAGE under reducing conditions.

8. A pharmaceutical composition comprising a polypeptide according to claim 7 in a pharmaceutically-acceptable diluent, adjuvant, or carrier.

9. A method of modulating the activity of human Flt4 receptor tyrosine kinase comprising administering to a person in need of modulation of Flt4 receptor tyrosine kinase activity a composition according to claim 8.

10. A purified and isolated polypeptide according to claim 7 that binds Flt4 and stimulates Flt4 phosphorylation in mammalian cells expressing Flt4.

11. A method of modulating the activity of human Flt4 receptor tyrosine kinase comprising contacting cells that express human Flt4 receptor tyrosine kinase with a polypeptide according to claim 10.

12. A purified and isolated polypeptide according to claim 10, said polypeptide comprising an amino acid sequence set forth in SEQ ID NO: 13.

13. A polypeptide according to claim 7 further comprising a detectable label.

14. A polypeptide according to claim 7 wherein said portion of SEQ ID NO: 33 effective to permit such binding is a continuous portion of SEQ ID NO: 33 within amino acids 1–180 of SEQ ID NO: 33.

15. A polypeptide according to claim 7 wherein the amino terminus of said portion effective to permit such binding corresponds with position 34 of SEQ ID NO: 33.

16. A method of modulating the activity of human Flt4 receptor tyrosine kinase comprising contacting cells that express human Flt4 receptor tyrosine kinase with a polypeptide according to claim 7.

17. A purified and isolated polypeptide comprising a human polypeptide capable of binding with high affinity to the extracellular domain of Flt4 receptor tyrosine kinase and having an apparent molecular weight of approximately 23 kD as assessed by SDS-PAGE under reducing conditions, wherein amino terminal amino acids 2 through 18 of said human polypeptide have an amino acid sequence corresponding to amino acids 2 through 18 set forth in SEQ ID NO: 13.

18. A method of modulating the activity of human Flt4 receptor tyrosine kinase comprising contacting cells that express human Flt4 receptor tyrosine kinase with a polypeptide according to claim 17.

19. A purified and isolated polypeptide according to claim 17 that binds Flt4 and stimulates Flt4 phosphorylation in mammalian cells expressing Flt4.

20. A pharmaceutical composition comprising a polypeptide according to claim 17 in a pharmaceutically-acceptable diluent, adjuvant, or carrier.

21. A method of modulating the activity of human Flt4 receptor tyrosine kinase comprising administering to a person in need of modulation of Flt4 receptor tyrosine kinase activity a composition according to claim 20.

22. A polypeptide according to claim 17 further comprising a detectable label.

23. A purified and isolated polypeptide capable of binding with high affinity to the extracellular domain of Flt4 receptor tyrosine kinase, wherein said polypeptide has an apparent molecular weight of approximately 23 kD as assessed by SDS-PAGE under reducing conditions and is purifyable from conditioned media from a PC-3 prostatic adenocarcinoma cell line, said cell line having ATCC CRL No. 1435, using an affinity purification procedure wherein the affinity purification matrix comprises a polypeptide comprising the extracellular domain of Flt4 receptor tyrosine kinase.

24. A polypeptide according to claim 23 which is capable of stimulating Flt4 phosphorylation in mammalian cells expressing Flt4 receptor tyrosine kinase.

25. A method of modulating the activity of human Flt4 receptor tyrosine kinase comprising contacting cells that express human Flt4 receptor tyrosine kinase with a polypeptide according to claim 24.

26. A polypeptide according to claim 23 further comprising a detectable label.

27. A pharmaceutical composition comprising a polypeptide according to claim 23 in a pharmaceutically-acceptable diluent, adjuvant, or carrier.

28. A method of modulating the activity of human Flt4 receptor tyrosine kinase comprising administering to a person in need of modulation of Flt4 receptor tyrosine kinase activity a composition according to claim 27.

29. A method of modulating the activity of human Flt4 receptor tyrosine kinase comprising contacting cells that express human Flt4 receptor tyrosine kinase with a polypeptide according to claim 23.

\* \* \* \* \*

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

TGTCCTCGCT GTCCTTGTCT                                                    20

(2) INFORMATION FOR SEQ ID NO: 2:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

ACATGCATGC CACCATGCAG CGGGGCGCCG CGCTGTGCCT GCGACTGTGG CTCTGCCTGG         60

GACTCCTGGA                                                               70

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ACATGCATGC CCCGCCGGTC ATCC                                               24

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CGGAATTCCC CATGACCCCA AC                                                 22

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CCATCGATGG ATCCTACCTG AAGCCGCTTT CTT                                     33

(2) INFORMATION FOR SEQ ID NO: 6:

(i) SEQUENCE CHARACTERISTICS:
        (A) LENGTH: 17 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 6:

ATTTAGGTGA CACTATA                                                              17

(2) INFORMATION FOR SEQ ID NO: 7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CCATCGATGG ATCCCGATGC TGCTTAGTAG CTGT                                            34

(2) INFORMATION FOR SEQ ID NO: 8:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Pro Met Thr Pro Thr Thr Tyr Lys Gly Ser Val Asp Asn Gln Thr As
1               5                   10                  15

Ser Gly Met Val Leu Ala Ser Glu Glu Phe Glu Gln Ile Glu Ser Ar
            20                  25                  30

His Arg Gln Glu Ser Gly Phe Arg
            35                  40

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CTGGAGTCGA CTTGGCGGAC T                                                         21

(2) INFORMATION FOR SEQ ID NO: 10:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CGCGGATCCC TAGTGATGGT GATGGTGATG TCTACCTTCG ATCATGCTGC CCTTATCCTC               60

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CCCAAGCTTG GATCCAAGTG GCTACTCCAT GACC                    34

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GTTGCCTGTG ATGTGCACCA                                    20

(2) INFORMATION FOR SEQ ID NO: 13:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Xaa Glu Glu Thr Ile Lys Phe Ala Ala Ala His Tyr Asn Thr Glu Il
1               5                   10                  15

Leu Lys (2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GCAGARGARA CNATHAA                                       17

(2) INFORMATION FOR SEQ ID NO: 15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

Glu Glu Thr Ile Lys
1               5

(2) INFORMATION FOR SEQ ID NO: 16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

GCAYTTNARD ATYTCNGT                                                    18

(2) INFORMATION FOR SEQ ID NO: 17:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 17:

Thr Glu Ile Leu Lys
1               5

(2) INFORMATION FOR SEQ ID NO: 18:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 18:

ATTCGCTGCA GCACACTACA AC                                               22

(2) INFORMATION FOR SEQ ID NO: 19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 19:

TCAGTGTTGT AGTGTGCTG                                                   19

(2) INFORMATION FOR SEQ ID NO: 20:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 20:

Ala Ala His Tyr Asn Thr Glu
1               5

(2) INFORMATION FOR SEQ ID NO: 21:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 21:

TAATACGACT CACTATAGGG                                               20

(2) INFORMATION FOR SEQ ID NO: 22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 22:

GTTGTAGTGT GCTGCAGCGA ATTT                                          24

(2) INFORMATION FOR SEQ ID NO: 23:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

Lys Phe Ala Ala Ala His Tyr Asn
1               5

(2) INFORMATION FOR SEQ ID NO: 24:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 24:

TCACTATAGG GAGACCCAAG C                                             21

(2) INFORMATION FOR SEQ ID NO: 25:

(i) SEQUENCE CHARACTERISTICS:
            (A) LENGTH: 219 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 25:

TCACTATAGG GAGACCCAAG CTTGGTACCG AGCTCGGATC CACTAGTAAC GGCCGCCAGT    60

GTGGTGGAAT TCGACGAACT CATGACTGTA CTCTACCCAG AATATTGGAA AATGTACAA    120

TGTCAGCTAA GGCAAGGAGG CTGGCAACAT AACAGAGAAC AGGCCAACCT CAACTCAAG    180

ACAGAAGAGA CTATAAAATT CGCTGCAGCA CACTACAAC                         219

(2) INFORMATION FOR SEQ ID NO: 26:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 26:

ACAGAGAACA GGCCAACC                                                        18

(2) INFORMATION FOR SEQ ID NO: 27:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 27:

TCTAGCATTT AGGTGACAC                                                       19

(2) INFORMATION FOR SEQ ID NO: 28:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 28:

AAGAGACTAT AAAATTCGCT GCAGC                                                25

(2) INFORMATION FOR SEQ ID NO: 29:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 29:

CCCTCTAGAT GCATGCTCGA                                                      20

(2) INFORMATION FOR SEQ ID NO: 30:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 30:

GTTGTAGTGT GCTGCAGCGA ATTT                                                 24

(2) INFORMATION FOR SEQ ID NO: 31:

(i) SEQUENCE CHARACTERISTICS:
       (A) LENGTH: 21 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 31:

```
TCACTATAGG GAGACCCAAG C                                              21
```

(2) INFORMATION FOR SEQ ID NO: 32:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 37..1089

(xi) SEQUENCE DESCRIPTION: SEQ ID NO: 32:

```
GAGCAGTTAC GGTCTGTGTC CAGTGTAGAT GAACTC ATG ACT GTA CTC TAC CCA          54
                                     Met Thr Val Leu Tyr Pro
                                       1               5

GAA TAT TGG AAA ATG TAC AAG TGT CAG CTA AGG AAA GGA GGC TGG CAA         102
Glu Tyr Trp Lys Met Tyr Lys Cys Gln Leu Arg Lys Gly Gly Trp Gln
            10                  15                  20

CAT AAC AGA GAA CAG GCC AAC CTC AAC TCA AGG ACA GAA GAG ACT ATA         150
His Asn Arg Glu Gln Ala Asn Leu Asn Ser Arg Thr Glu Glu Thr Ile
        25                  30                  35

AAA TTT GCT GCA GCA CAT TAT AAT ACA GAG ATC TTG AAA AGT ATT GAT         198
Lys Phe Ala Ala Ala His Tyr Asn Thr Glu Ile Leu Lys Ser Ile Asp
    40                  45                  50

AAT GAG TGG AGA AAG ACT CAA TGC ATG CCA CGG GAG GTG TGT ATA GAT         246
Asn Glu Trp Arg Lys Thr Gln Cys Met Pro Arg Glu Val Cys Ile Asp
55                  60                  65                  70

GTG GGG AAG GAG TTT GGA GTC GCG ACA AAC ACC TTC TTT AAA CCT CCA         294
Val Gly Lys Glu Phe Gly Val Ala Thr Asn Thr Phe Phe Lys Pro Pro
            75                  80                  85

TGT GTG TCC GTC TAC AGA TGT GGG GGT TGC TGC AAT AGT GAG GGG CTG         342
Cys Val Ser Val Tyr Arg Cys Gly Gly Cys Cys Asn Ser Glu Gly Leu
            90                  95                 100

CAG TGC ATG AAC ACC AGC ACG AGC TAC CTC AGC AAG ACG TTA TTT GAA         390
Gln Cys Met Asn Thr Ser Thr Ser Tyr Leu Ser Lys Thr Leu Phe Glu
        105                 110                 115

ATT ACA GTG CCT CTC TCT CAA GGC CCC AAA CCA GTA ACA ATC AGT TTT         438
Ile Thr Val Pro Leu Ser Gln Gly Pro Lys Pro Val Thr Ile Ser Phe
120                 125                 130

GCC AAT CAC ACT TCC TGC CGA TGC ATG TCT AAA CTG GAT GTT TAC AGA         486
Ala Asn His Thr Ser Cys Arg Cys Met Ser Lys Leu Asp Val Tyr Arg
135                 140                 145                 150

CAA GTT CAT TCC ATT ATT AGA CGT TCC CTG CCA GCA ACA CTA CCA CAG         534
Gln Val His Ser Ile Ile Arg Arg Ser Leu Pro Ala Thr Leu Pro Gln
            155                 160                 165

TGT CAG GCA GCG AAC AAG ACC TGC CCC ACC AAT TAC ATG TGG AAT AAT         582
Cys Gln Ala Ala Asn Lys Thr Cys Pro Thr Asn Tyr Met Trp Asn Asn
        170                 175                 180

CAC ATC TGC AGA TGC CTG GCT CAG GAA GAT TTT ATG TTT TCC TCG GAT         630
His Ile Cys Arg Cys Leu Ala Gln Glu Asp Phe Met Phe Ser Ser Asp
        185                 190                 195
```

```
GCT GGA GAT GAC TCA ACA GAT GGA TTC CAT GAC ATC TGT GGA CCA AAC      678
Ala Gly Asp Asp Ser Thr Asp Gly Phe His Asp Ile Cys Gly Pro Asn
200                 205                 210

AAG GAG CTG GAT GAA GAG ACC TGT CAG TGT GTC TGC AGA GCG GGG CTT      726
Lys Glu Leu Asp Glu Glu Thr Cys Gln Cys Val Cys Arg Ala Gly Leu
215                 220                 225                 230

CGG CCT GCC AGC TGT GGA CCC CAC AAA GAA CTA GAC AGA AAC TCA TGC      774
Arg Pro Ala Ser Cys Gly Pro His Lys Glu Leu Asp Arg Asn Ser Cys
                235                 240                 245

CAG TGT GTC TGT AAA AAC AAA CTC TTC CCC AGC CAA TGT GGG GCC AAC      822
Gln Cys Val Cys Lys Asn Lys Leu Phe Pro Ser Gln Cys Gly Ala Asn
                250                 255                 260

CGA GAA TTT GAT GAA AAC ACA TGC CAG TGT GTA TGT AAA AGA ACC TGC      870
Arg Glu Phe Asp Glu Asn Thr Cys Gln Cys Val Cys Lys Arg Thr Cys
                265                 270                 275

CCC AGA AAT CAA CCC CTA AAT CCT GGA AAA TGT GCC TGT GAA TGT ACA      918
Pro Arg Asn Gln Pro Leu Asn Pro Gly Lys Cys Ala Cys Glu Cys Thr
280                 285                 290

GAA AGT CCA CAG AAA TGC TTG TTA AAA GGA AAG AAG TTC CAC CAC CAA      966
Glu Ser Pro Gln Lys Cys Leu Leu Lys Gly Lys Lys Phe His His Gln
295                 300                 305                 310

ACA TGC AGC TGT TAC AGA CGG CCA TGT ACG AAC CGC CAG AAG GCT TGT     1014
Thr Cys Ser Cys Tyr Arg Arg Pro Cys Thr Asn Arg Gln Lys Ala Cys
                315                 320                 325

GAG CCA GGA TTT TCA TAT AGT GAA GAA GTG TGT CGT TGT GTC CCT TCA     1062
Glu Pro Gly Phe Ser Tyr Ser Glu Glu Val Cys Arg Cys Val Pro Ser
                330                 335                 340

TAT TGG AAA AGA CCA CAA ATG AGC TAAGATTGTA CTGTTTTCCA GTTCATCGA     1116
Tyr Trp Lys Arg Pro Gln Met Ser
                345                 350

TTTCTATTAT GGAAAACTGT GTTG                                          1140

(2) INFORMATION FOR SEQ ID NO: 33:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO: 33:

Met Thr Val Leu Tyr Pro Glu Tyr Trp Lys Met Tyr Lys Cys Gln Leu
1               5                   10                  15

Arg Lys Gly Gly Trp Gln His Asn Arg Glu Gln Ala Asn Leu Asn Ser
                20                  25                  30

Arg Thr Glu Glu Thr Ile Lys Phe Ala Ala His Tyr Asn Thr Glu
            35                  40                  45

Ile Leu Lys Ser Ile Asp Asn Glu Trp Arg Lys Thr Gln Cys Met Pro
        50                  55                  60

Arg Glu Val Cys Ile Asp Val Gly Lys Glu Phe Gly Val Ala Thr Asn
65                  70                  75                  80

Thr Phe Phe Lys Pro Pro Cys Val Ser Val Tyr Arg Cys Gly Cys
                85                  90                  95

Cys Asn Ser Glu Gly Leu Gln Cys Met Asn Thr Ser Thr Ser Tyr Leu
                100                 105                 110

Ser Lys Thr Leu Phe Glu Ile Thr Val Pro Leu Ser Gln Gly Pro Lys
            115                 120                 125

Pro Val Thr Ile Ser Phe Ala Asn His Thr Ser Cys Arg Cys Met Ser
```

```
            130                 135                 140
Lys Leu Asp Val Tyr Arg Gln Val His Ser Ile Ile Arg Arg Ser Leu
145                 150                 155                 160

Pro Ala Thr Leu Pro Gln Cys Gln Ala Ala Asn Lys Thr Cys Pro Thr
                165                 170                 175

Asn Tyr Met Trp Asn Asn His Ile Cys Arg Cys Leu Ala Gln Glu Asp
            180                 185                 190

Phe Met Phe Ser Ser Asp Ala Gly Asp Asp Ser Thr Asp Gly Phe His
            195                 200                 205

Asp Ile Cys Gly Pro Asn Lys Glu Leu Asp Glu Thr Cys Gln Cys
            210                 215                 220

Val Cys Arg Ala Gly Leu Arg Pro Ala Ser Cys Gly Pro His Lys Glu
225                 230                 235                 240

Leu Asp Arg Asn Ser Cys Gln Cys Val Cys Lys Asn Lys Leu Phe Pro
                245                 250                 255

Ser Gln Cys Gly Ala Asn Arg Glu Phe Asp Glu Asn Thr Cys Gln Cys
                260                 265                 270

Val Cys Lys Arg Thr Cys Pro Arg Asn Gln Pro Leu Asn Pro Gly Lys
            275                 280                 285

Cys Ala Cys Glu Cys Thr Glu Ser Pro Gln Lys Cys Leu Leu Lys Gly
290                 295                 300

Lys Lys Phe His His Gln Thr Cys Ser Cys Tyr Arg Arg Pro Cys Thr
305                 310                 315                 320

Asn Arg Gln Lys Ala Cys Glu Pro Gly Phe Ser Tyr Ser Glu Glu Val
                325                 330                 335

Cys Arg Cys Val Pro Ser Tyr Trp Lys Arg Pro Gln Met Ser
                340                 345                 350

(2) INFORMATION FOR SEQ ID NO: 34:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 352..1608

(xi) SEQUENCE DESCRIPTION: SEQ ID NO: 34:

CCCGCCCCGC CTCTCCAAAA AGCTACACCG ACGCGGACCG CGGCGGCGTC CTCCCTCGCC      60

CTCGCTTCAC CTCGCGGGCT CCGAATGCGG GGAGCTCGGA TGTCCGGTTT CCTGTGAGG     120

TTTTACCTGA CACCCGCCGC CTTTCCCCGG CACTGGCTGG GAGGGCGCCC TGCAAAGTT    180

GGAACGCGGA GCCCCGGACC CGCTCCCGCC GCCTCCGGCT CGCCCAGGGG GGGTCGCCG    240

GAGGAGCCCG GGGAGAGGG ACCAGGAGGG GCCCGCGGCC TCGCAGGGGC GCCCGCGCC     300

CCACCCCTGC CCCCGCCAGC GGACCGGTCC CCCACCCCCG GTCCTTCCAC C ATG CAC    357
                                                          Met His
                                                            1

TTG CTG GGC TTC TTC TCT GTG GCG TGT TCT CTG CTC GCC GCT GCG CTG    405
Leu Leu Gly Phe Phe Ser Val Ala Cys Ser Leu Leu Ala Ala Ala Leu
      5                  10                  15

CTC CCG GGT CCT CGC GAG GCG CCC GCC GCC GCC GCC TTC GAG TCC        453
Leu Pro Gly Pro Arg Glu Ala Pro Ala Ala Ala Ala Phe Glu Ser
    20                  25                  30
```

```
GGA CTC GAC CTC TCG GAC GCG GAG CCC GAC GCG GGC GAG GCC ACG GCT      501
Gly Leu Asp Leu Ser Asp Ala Glu Pro Asp Ala Gly Glu Ala Thr Ala
 35              40                  45                  50

TAT GCA AGC AAA GAT CTG GAG GAG CAG TTA CGG TCT GTG TCC AGT GTA      549
Tyr Ala Ser Lys Asp Leu Glu Glu Gln Leu Arg Ser Val Ser Ser Val
                 55                  60                  65

GAT GAA CTC ATG ACT GTA CTC TAC CCA GAA TAT TGG AAA ATG TAC AAG      597
Asp Glu Leu Met Thr Val Leu Tyr Pro Glu Tyr Trp Lys Met Tyr Lys
             70                  75                  80

TGT CAG CTA AGG AAA GGA GGC TGG CAA CAT AAC AGA GAA CAG GCC AAC      645
Cys Gln Leu Arg Lys Gly Gly Trp Gln His Asn Arg Glu Gln Ala Asn
         85                  90                  95

CTC AAC TCA AGG ACA GAA GAG ACT ATA AAA TTT GCT GCA GCA CAT TAT      693
Leu Asn Ser Arg Thr Glu Glu Thr Ile Lys Phe Ala Ala Ala His Tyr
     100                 105                 110

AAT ACA GAG ATC TTG AAA AGT ATT GAT AAT GAG TGG AGA AAG ACT CAA      741
Asn Thr Glu Ile Leu Lys Ser Ile Asp Asn Glu Trp Arg Lys Thr Gln
115                 120                 125                 130

TGC ATG CCA CGG GAG GTG TGT ATA GAT GTG GGG AAG GAG TTT GGA GTC      789
Cys Met Pro Arg Glu Val Cys Ile Asp Val Gly Lys Glu Phe Gly Val
                 135                 140                 145

GCG ACA AAC ACC TTC TTT AAA CCT CCA TGT GTG TCC GTC TAC AGA TGT      837
Ala Thr Asn Thr Phe Phe Lys Pro Pro Cys Val Ser Val Tyr Arg Cys
             150                 155                 160

GGG GGT TGC TGC AAT AGT GAG GGG CTG CAG TGC ATG AAC ACC AGC ACG      885
Gly Gly Cys Cys Asn Ser Glu Gly Leu Gln Cys Met Asn Thr Ser Thr
         165                 170                 175

AGC TAC CTC AGC AAG ACG TTA TTT GAA ATT ACA GTG CCT CTC TCT CAA      933
Ser Tyr Leu Ser Lys Thr Leu Phe Glu Ile Thr Val Pro Leu Ser Gln
     180                 185                 190

GGC CCC AAA CCA GTA ACA ATC AGT TTT GCC AAT CAC ACT TCC TGC CGA      981
Gly Pro Lys Pro Val Thr Ile Ser Phe Ala Asn His Thr Ser Cys Arg
195                 200                 205                 210

TGC ATG TCT AAA CTG GAT GTT TAC AGA CAA GTT CAT TCC ATT ATT AGA     1029
Cys Met Ser Lys Leu Asp Val Tyr Arg Gln Val His Ser Ile Ile Arg
                 215                 220                 225

CGT TCC CTG CCA GCA ACA CTA CCA CAG TGT CAG GCA GCG AAC AAG ACC     1077
Arg Ser Leu Pro Ala Thr Leu Pro Gln Cys Gln Ala Ala Asn Lys Thr
             230                 235                 240

TGC CCC ACC AAT TAC ATG TGG AAT AAT CAC ATC TGC AGA TGC CTG GCT     1125
Cys Pro Thr Asn Tyr Met Trp Asn Asn His Ile Cys Arg Cys Leu Ala
         245                 250                 255

CAG GAA GAT TTT ATG TTT TCC TCG GAT GCT GGA GAT GAC TCA ACA GAT     1173
Gln Glu Asp Phe Met Phe Ser Ser Asp Ala Gly Asp Asp Ser Thr Asp
     260                 265                 270

GGA TTC CAT GAC ATC TGT GGA CCA AAC AAG GAG CTG GAT GAA GAG ACC     1221
Gly Phe His Asp Ile Cys Gly Pro Asn Lys Glu Leu Asp Glu Glu Thr
275                 280                 285                 290

TGT CAG TGT GTC TGC AGA GCG GGG CTT CGG CCT GCC AGC TGT GGA CCC     1269
Cys Gln Cys Val Cys Arg Ala Gly Leu Arg Pro Ala Ser Cys Gly Pro
                 295                 300                 305

CAC AAA GAA CTA GAC AGA AAC TCA TGC CAG TGT GTC TGT AAA AAC AAA     1317
His Lys Glu Leu Asp Arg Asn Ser Cys Gln Cys Val Cys Lys Asn Lys
             310                 315                 320

CTC TTC CCC AGC CAA TGT GGG GCC AAC CGA GAA TTT GAT GAA AAC ACA     1365
Leu Phe Pro Ser Gln Cys Gly Ala Asn Arg Glu Phe Asp Glu Asn Thr
         325                 330                 335

TGC CAG TGT GTA TGT AAA AGA ACC TGC CCC AGA AAT CAA CCC CTA AAT     1413
Cys Gln Cys Val Cys Lys Arg Thr Cys Pro Arg Asn Gln Pro Leu Asn
```

-continued

```
       340                 345                 350
CCT GGA AAA TGT GCC TGT GAA TGT ACA GAA AGT CCA CAG AAA TGC TTG    1461
Pro Gly Lys Cys Ala Cys Glu Cys Thr Glu Ser Pro Gln Lys Cys Leu
355                 360                 365                 370

TTA AAA GGA AAG AAG TTC CAC CAC CAA ACA TGC AGC TGT TAC AGA CGG    1509
Leu Lys Gly Lys Lys Phe His His Gln Thr Cys Ser Cys Tyr Arg Arg
            375                 380                 385

CCA TGT ACG AAC CGC CAG AAG GCT TGT GAG CCA GGA TTT TCA TAT AGT    1557
Pro Cys Thr Asn Arg Gln Lys Ala Cys Glu Pro Gly Phe Ser Tyr Ser
            390                 395                 400

GAA GAA GTG TGT CGT TGT GTC CCT TCA TAT TGG AAA AGA CCA CAA ATG    1605
Glu Glu Val Cys Arg Cys Val Pro Ser Tyr Trp Lys Arg Pro Gln Met
            405                 410                 415

AGC TAAGATTGTA CTGTTTTCCA GTTCATCGAT TTTCTATTAT GGAAAACTGT         1658
Ser

GTTGCCACAG TAGAACTGTC TGTGAACAGA GAGACCCTTG TGGGTCCATG CTAACAAA    1718

CAAAAGTCTG TCTTTCCTGA ACCATGTGGA TAACTTTACA GAAATGGACT GGAGCTCA    1778

TGCAAAAGGC CTCTTGTAAA GACTGGTTTT CTGCCAATGA CCAAACAGCC AAGATTTT    1838

TCTTGTGATT TCTTTAAAAG AATGACTATA TAATTTATTT CCACTAAAAA TATTGTTT    1898

GCATTCATTT TTATAGCAAC AACAATTGGT AAAACTCACT GTGATCAATA TTTTTATA    1958

ATGCAAAATA TGTTTAAAAT AAAATGAAAA TTGTATTAT                         1997

(2) INFORMATION FOR SEQ ID NO: 35:

(i) SEQUENCE CHARACTERISTICS:
           (A) LENGTH: 419 amino acids
           (B) TYPE: amino acid
           (D) TOPOLOGY: linear (ii) MOLECULE TYPE: protein (xi) SEQUENCE DESCRIPTION: SEQ ID NO: 35:

Met His Leu Leu Gly Phe Phe Ser Val Ala Cys Ser Leu Leu Ala Ala
 1               5                  10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
```

-continued

```
                    180                 185                 190
Ser Gln Gly Pro Lys Pro Val Thr Ile Ser Phe Ala Asn His Thr Ser
        195                 200                 205
Cys Arg Cys Met Ser Lys Leu Asp Val Tyr Arg Gln Val His Ser Ile
    210                 215                 220
Ile Arg Arg Ser Leu Pro Ala Thr Leu Pro Gln Cys Gln Ala Ala Asn
225                 230                 235                 240
Lys Thr Cys Pro Thr Asn Tyr Met Trp Asn Asn His Ile Cys Arg Cys
                245                 250                 255
Leu Ala Gln Glu Asp Phe Met Phe Ser Ser Asp Ala Gly Asp Asp Ser
            260                 265                 270
Thr Asp Gly Phe His Asp Ile Cys Gly Pro Asn Lys Glu Leu Asp Glu
        275                 280                 285
Glu Thr Cys Gln Cys Val Cys Arg Ala Gly Leu Arg Pro Ala Ser Cys
    290                 295                 300
Gly Pro His Lys Glu Leu Asp Arg Asn Ser Cys Gln Cys Val Cys Lys
305                 310                 315                 320
Asn Lys Leu Phe Pro Ser Gln Cys Gly Ala Asn Arg Glu Phe Asp Glu
                325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
        355                 360                 365
Cys Leu Leu Lys Gly Lys Lys Phe His His Gln Thr Cys Ser Cys Tyr
    370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Lys Arg Pro
                405                 410                 415
Gln Met Ser
```